United States Patent [19]

Donate et al.

[11] Patent Number: 4,486,614

[45] Date of Patent: Dec. 4, 1984

[54] ANIONIC POLYMERIZATION OF CIS- AND TRANS-1,3-PENTADIENE FROM A MIXTURE OF SATURATED AND UNSATURATED HYDROCARBONS

[75] Inventors: Felipe A. Donate; John W. Bozzelli; Kent S. Dennis, all of Midland, Mich.

[73] Assignee: The Dow Chemical Company, Midland, Mich.

[21] Appl. No.: 517,171

[22] Filed: Jul. 25, 1983

[51] Int. Cl.$^3$ .............................. C07C 1/16; C07C 2/74
[52] U.S. Cl. ......................................... 585/10; 585/18; 585/255; 585/507; 585/520
[58] Field of Search ................. 585/255, 507, 520, 10, 585/18; 526/173

[56] References Cited

U.S. PATENT DOCUMENTS

| | | | |
|---|---|---|---|
| 2,023,793 | 12/1935 | Scott | 260/168 |
| 2,398,973 | 4/1946 | Suday | 260/681.5 |
| 2,985,594 | 5/1961 | Zimmerman | 252/431 |
| 3,105,828 | 10/1963 | Porter | 260/83.7 |
| 3,306,949 | 2/1967 | Mertzweiller et al. | 260/680 |
| 3,324,191 | 6/1967 | Wofford | 260/669 |
| 3,331,826 | 7/1967 | Talcott | 260/94.2 |
| 3,360,580 | 12/1967 | Mertzweiller et al. | 260/569 |
| 3,458,491 | 7/1969 | Dennis | 260/94.2 |
| 3,505,304 | 4/1970 | Davidson et al. | 260/94.2 |
| 3,577,398 | 5/1971 | Pace et al. | 260/85.3 |
| 3,647,913 | 3/1972 | Lasis | 260/681.5 |
| 3,789,090 | 1/1974 | Otsuki et al. | 260/669 P |
| 3,792,105 | 2/1974 | Siegmann | 260/681.5 R |
| 4,060,492 | 11/1977 | Yasui | 252/59 |
| 4,313,019 | 1/1982 | Hara et al. | 585/429 |
| 4,337,329 | 6/1982 | Kubo et al. | 525/339 |

FOREIGN PATENT DOCUMENTS

| | | |
|---|---|---|
| 7343082 | 9/1969 | Japan . |
| 7209848 | 7/1972 | Netherlands . |
| 2092163 | 8/1982 | United Kingdom . |
| 670578 | of 0000 | U.S.S.R. . |

OTHER PUBLICATIONS

"Chain Transfer in Anionic Polymerization", A. L. Gatzke, Journal of Polymer Science, Part A-1, vol. 7, 2281-2292 (1969).

*Primary Examiner*—Curtis R. Davis
*Attorney, Agent, or Firm*—D. R. Howard

[57] ABSTRACT

1,3-pentadiene is polymerized from a mixture of saturated and unsaturated hydrocarbon compounds, the compounds having primarily 5 carbon atoms per molecule, with an anionic polymerization initiator. The mixture of saturated and unsaturated hydrocarbon compounds is contacted, in an inert atmosphere, with an anionic polymerization initiator to form a reaction mixture. The anionic polymerization initiator is present in an amount sufficient to inactivate polymerization-terminating compounds present in the mixture and to initiate polymerization of 1,3-pentadiene from the mixture. The reaction mixture is heated with stirring to a temperature sufficient to inactivate the polymerization terminating compounds. After inactivation of the polymerization terminating compounds, the reaction mixture is then heated with stirring to a temperature sufficient to initiate polymerization of 1,3-pentadiene from the reaction mixture. Polymer recovery and subsequent functionalization, if any, follow thereafter.

27 Claims, No Drawings

4,486,614

ANIONIC POLYMERIZATION OF CIS- AND TRANS-1,3-PENTADIENE FROM A MIXTURE OF SATURATED AND UNSATURATED HYDROCARBONS

BACKGROUND OF THE INVENTION

This invention relates generally to anionic polymerization of 1,3-pentadiene (piperylene). The 1,3-pentadiene is generally in admixture with other saturated and unsaturated hydrocarbons containing 5 carbon atoms. One source of such an admixture is a 5-carbon distillation cut obtained from a cracking of petroleum. This invention also relates to polymers of 1,3-pentadiene so prepared. This invention further relates to hydrogenated polymers of 1,3-pentadiene.

First, anionic polymerization of conjugated dienes is known. Second, several anionic polymerization catalysts or initiators are known. Third, chain transfer agents and/or polar solvents have been used in some anionic polymerizations. Fourth, conjugated dienes in general, and linear conjugated dienes having 4 to 6 carbon atoms per molecule in particular, are generally thought to be equally suitable for purposes of the aforementioned references. Fifth, a pure or substantially pure diolefin feed stream is preferred. Other than those references which teach copolymerization of a conjugated diene with either another conjugated diolefin or a vinyl compound, only U.S. Pat. No. 3,505,304 to Davison et al. discloses preparation of polymers from an impure hydrocarbon fraction. Polymers so produced are generally rubbery polymers. Sixth, polymers prepared in accordance with the foregoing references may, depending upon the polymerization components and conditions, range from liquid polymers to solid polymers with a variety of molecular weights and molecular weight distributions.

In copending Application Ser. No. 455,146, filed Jan. 3, 1983, and now abandoned, is taught that 1,3-pentadiene is selectively polymerized from a mixture of saturated and unsaturated hydrocarbon compounds. The compounds have primarily 5 carbon atoms per molecule. Polymerization is effected by using an anionic polymerization initiator in conjunction with a polar solvent. Active hydrogen compounds and polymerization-terminating compounds may be inactivated and separated from the mixture of hydrocarbon compounds before starting polymerization. As an alternative, inactivation and separation of active hydrogen compounds and polymerization-terminating compounds may be omitted provided the anionic polymerization initiator is employed in an amount to (a) inactivate such compounds and (b) initiate polymerization of 1,3-pentadiene.

SUMMARY OF THE INVENTION

It has now been found that 1,3-pentadiene is polymerized from a mixture of saturated and unsaturated hydrocarbon compounds, the compounds having primarily 5 carbon atoms per molecule, using only an anionic polymerization initiator provided certain conditions are met.

A first condition is that polymerization of 1,3-pentadiene must be conducted in an inert gaseous atmosphere. As used herein, "inert" means that no detectable reaction is observed with respect to components of the mixture, the polymerization initiator or polymerized 1,3-pentadiene.

A second condition is that temperature must be controlled in such a manner that if not all, polymerization terminating compounds such as alpha-alkynes and cyclopentadiene are inactived before significant polymerization of 1,3-pentadiene commences. With certain initiators, such as sodium metal, a line of demarcation between completion of polymerization terminating compound inactivation and commencement of polymerization of 1,3-pentadiene is observable. With other initiators, such as potassium metal, inactivation of polymerization terminating compounds and commencement of polymerization of 1,3-pentadiene appear to occur almost simultaneously, making observation of a line of demarcation difficult. Notwithstanding such difficulty, it is believed that inactivation of polymerization terminating compounds still precedes polymerization of 1,3-pentadiene.

A third condition is that the anionic polymerization initiator should be dispersed throughout the mixture of saturated and unsaturated hydrocarbons for most efficient polymerization of 1,3-pentadiene from the mixture. If the initiator is soluble in the mixture, no agitation is required to disperse the initiator. If the initiator is not soluble in the mixture, an external agiation means must be used to provide adequate dispersion of the initiator.

In one aspect, the present invention is a method for anionically preparing polymers of 1,3-pentadiene from a distillation cut available as a by-product of crude oil cracking operations, said distillation cut being a mixture of saturated and unsaturated hydrocarbon molecules, at least 50 percent by weight of said molecules having 5 carbon atoms per molecule, said mixture comprising cis-1,3-pentadiene, trans-1,3-pentadiene, cyclopentadiene and other 5-carbon atom molecules, the method comprising:

(a) forming a reaction mixture by contacting, in an inert atmosphere, the mixture of saturated and unsaturated hydrocarbon molecules with an amount of an anionic polymerization initiator sufficient to: (i) inactivate the chain termination function of generally all cyclopentadiene contained in the mixture; and (ii) initiate polymerization of 1,3-pentadiene;

(b) heating the reaction mixture to a first temperature, said first temperature being sufficiently high to cause the cyclopentadiene contained in the reaction mixture to react with the initiator to form a reaction product which does not interfere with polymerization of 1,3-pentadiene and maintaining dispersal of the initiator throughout the reaction mixture for a period of time sufficient to inactivate more than about 90 percent of the cyclopentadiene contained in the reaction mixture; and (c) subsequent to inactivation of the cyclopentadiene, heating the reaction mixture to a second temperature, the second temperature being sufficiently high to initiate polymerization of 1,3-pentadiene, and maintaining dispersal of the initiator throughout the reaction mixture for a period of time sufficient to attain a desired polymer yield.

In a second aspect, the present invention is a method for anionically preparing polymers of 1,3-pentadiene from a distillation cut available as a by-product of crude oil cracking operations, said distillation cut being a mixture of saturated and unsaturated hydrocarbon molecules, at least 50 percent by weight of said molecules having 5-carbon atoms per molecule, said mixture comprising cis-1,3-pentadiene, trans-1,3-pentadiene, cyclopentadiene and other 5-carbon atom molecules, the method comprising:
  (a) forming a reaction mixture by contacting, in an inert atmosphere, the mixture of saturated and unsaturated hydrocarbon molecules with an amount of an alkali metal polymerization initiator, the amount being sufficient to (1) inactivate the chain termination function of generally all cyclopentadiene contained in the mixture and (2) initiate polymerization of 1,3-pentadiene, the alkali metal polymerization initiator having a melting point; and
  (b) heating the reaction mixture to a temperature, the temperature being (1) greater than or equal to the melting point of the alkali metal polymerization initiator and (2) sufficient to initiate polymerization of 1,3-pentadiene, and dispersing the alkali metal initiator throughout the reaction mixture for a period of time sufficient to attain a desired polymer yield.

In a third aspect, the present invention is a method for anionically preparing polymers of 1,3-pentadiene from a distillation cut available as a by-product of crude oil cracking operations, said distillation cut being a mixture of saturated and unsaturated hydrocarbon molecules, at least 50 percent by weight of said molecules having 5-carbon atoms per molecule, said mixture comprising cis-1,3-pentadiene, trans-1,3-pentadiene, cyclopentadiene and other 5-carbon atom molecules, the method comprising:
  (a) melting, in an inert atmosphere, an amount of an alkali metal polymerization initiator, the initiator having a melting point and being selected from the group consisting of sodium and potassium, the amount being sufficient to (1) inactivate chain termination functions of generally all cyclopentadiene contained in the distillation cut and (2) initiate polymerization of the 1,3-pentadiene contained in the distillation cut;
  (b) heating the distillation cut, in an inert atmosphere, to a temperature, the temperature being greater than or equal to the melting point of the initiator;
  (c) dispersing the molten initiator throughout the heated distillation cut to thereby initiate polymerization of 1,3-pentadiene; and
  (d) maintaining dispersion of the initiator throughout the heated distillation cut for a period of time sufficient to attain a desired polymer yield, the heated distillation cut being maintained at a temperature greater than or equal to the melting point of the initiator.

Also within the scope of the present invention is the polymer of 1,3-pentadiene so formed.

In another aspect, the present invention contemplates a hydrogenated polymer of 1,3-pentadiene produced by the aforementioned process. The hydrogenated polymer can be used, for example, as a synthetic lubricating oil or as a component of a formulated lubricating oil.

DESCRIPTION OF THE PREFERRED EMBODIMENTS

A polymerization stock, or starting material, suitable for purposes of this invention is a $C_5$ stream, or distillation cut, available as a byproduct of crude oil refining or cracking operations. The $C_5$ cut is a distillation fraction composed of saturated and unsaturated hydrocarbon molecules and, as used herein, means that, based upon weight of fraction, more than about 50 percent weight percent of said molecules contain five carbon atoms. Suitably, more than about 60 weight percent of said molecules contain five carbon atoms. Beneficially, more than about 70 weight percent of said molecules contain five carbon atoms. Desirably, more than about 80 weight percent of said molecules contain five carbon atoms. Preferably, more than about 85 weight percent of said hydrocarbon molecules contain five carbon atoms. Most, preferably, more than about 90 weight percent of said hydrocarbon molecules contain five carbon atoms.

Side streams relatively rich in olefins or diolefins are generally available as products of the refining and cracking operations. The amount of diolefins can be increased by suitable cracking of an appropriate cut of a desired boiling range and/or fractionation of side streams.

A fraction, or distillate cut, rich in diolefins such as 1,3-pentadiene can be used as a polymerization stock with or without removal of, or reducing the amount of, impurities or polymerization-terminating compounds, chain transfer agents and other undesirable compounds.

The following is a gas chromatograph analysis, expressed in terms of weight percent, based on weight of sample, of a typical impure $C_5$ refinery stream obtained by the cracking of naphtha:

| Component | Weight Percent Rounded (To nearest 0.1) |
|---|---|
| propylene | 0.17 |
| propane | 0.16 |
| butenes | 0.18 |
| 1,3-butadiene | 0.81 |
| n-butane | 0.05 |
| vinyl acetylene | 0.02 |
| ethyl acetylene | 0.05 |
| cis-butene-2 | 1.29 |
| 1,2-butadiene | 1.38 |
| 3-methylbutene-1 | 0.88 |
| isopentane | 1.87 |
| 1,4-pentadiene | 5.50 |
| butyne-2 | 1.74 |
| pentene-1 | 14.25 |
| 2-methylbutene-1 | 2.90 |
| n-pentane | 2.35 |
| isoprene | 20.38 |
| trans-pentene-2 | 3.28 |
| cis-pentene-2 | 2.19 |
| 2-methylbutene-2 | 1.64 |
| trans-1,3-pentadiene | 13.77 |
| cyclopentadiene | 5.58 |
| cis-1,3-pentadiene | 6.45 |
| cyclopentene | 8.78 |
| cyclopentane | 0.03 |
| 1,5-hexadiene | <0.01 |
| dicyclopentadiene | 2.19 |
| residue | 2.10 |
| | 100 wt % |

The preceding gas chromatographic analysis indicates the presence of diolefins other than 1,3-pentadiene. These diolefins will also polymerize, at least to some extent, under polymerization conditions suitable for polymerization of 1,3-pentadiene. It may be desirable to remove all or part of the diolefins other than 1,3-pentadiene prior to polymerization.

A gas chromatograph analysis, expressed in terms of weight percent (to the nearest 0.01) based on weight of sample, of a piperylene concentrate or $C_5$ refinery stream which has an increased amount of 1,3-pentadiene, is as follows:

| Component | Weight Percent |
| --- | --- |
| propane | <0.01 |
| isobutane | <0.01 |
| n-butane | <0.01 |
| neopentane | <0.01 |
| isobutene | <0.01 |
| butene-1 | <0.01 |
| trans-butene-2 | <0.01 |
| isopentane | <0.01 |
| cis-butene-2 | <0.01 |
| 3-methylbutene-1 | 0.05 |
| 1,3-butadiene | <0.01 |
| pentene-1 | 0.14 |
| 1,2-butadiene | <0.01 |
| cis- and trans-pentene-2 | <0.01 |
| 2-methylbutene-1 | 2.79 |
| 2-methylbutene-2 | 3.58 |
| 1,4-pentadiene | <0.01 |
| butyne-1 | 4.68 |
| $C_6H_{12}$, 4-methylpentene-2, methylpentene and $C_5H_{10}$ cyclopentene | 4.12 20.12 |
| butyne-2 and 2-methylpentene-1 | 2.56 |
| 1,5-hexadiene | 3.75 |
| $C_6H_{10}$ | 1.11 |
| cyclopentadiene | 2.56 |
| benzene | 0.48 |
| residue | 2.28 |
| isoprene | 3.65 |
| trans-1,3-pentadiene | 29.01 |
| cis-1,3-pentadiene | 17.77 |
| dicyclopentadiene | 1.16 |
| | ~100 wt % |

The present invention is applicable to mixtures such as the impure $C_5$ refinery stream and the piperylene concentrate as illustrated in the gas chromatograph analyses hereinbefore set forth. In order to be economically viable, the mixture must contain at least five percent by weight of 1,3-pentadiene, based on mixture weight. Mixtures containing from about 25 to about 95 weight percent of 1,3-pentadiene, based on mixture weight, are desirable because they contain more 1,3-pentadiene monomer to be polymerized. Mixtures containing from about 40 to about 60 weight percent of 1,3-pentadiene, based on mixture weight are preferred because of availability as well as 1,3-pentadiene content.

The present invention is also applicable to isolated fractions which contain only cis-1,3-pentadiene, or trans-1,3-pentadiene, or mixtures thereof. The isolated fractions are, however, difficult to obtain and expensive.

Piperylene concentrates and impure $C_5$ refinery streams may be purified by inactivating active hydrogen compounds and polymerization terminating compounds. Purification is accomplished by treatment with a finely dispersed alkali metal in a manner like that taught by Soday in U.S. Pat. No. 2,398,973. The presence or absence of active hydrogen compounds may be determined by the well-known Zerewitinoff method. For purposes of the present invention the alkali metal is suitably selected from the group consisting of lithium, sodium, potassium, sodium-potassium alloys, lithium-sodium and lithium-potassium alloys. Finely dispersed metallic sodium is particularly suited for purposes of the present invention.

Treatment of a $C_5$ fraction with finely dispersed metallic sodium results in an effective removal of sodium reactive inhibitors or polymerization terminating compounds such as cyclopentadiene, alpha-alkynes, oxygen compounds, sulfur and sulfur compounds and, within a narrow temperature range, allenes. See, Siegmann, U.S. Pat. No. 3,792,105, the teachings of which are incorporated herein by reference thereto.

In accordance with the present invention, an anionic polymerization initiator is selected from the group consisting of alkali metals, dispersions of a finely divided alkali metal in an aliphatic hydrocarbon, organo-alkali metal compounds, alkali metal hydrides and alkali metal aluminum hydrides.

The alkali metals suitable for use in purifying piperylene concentrates and impure $C_5$ refinery streams are also suitable for use as anionic polymerization initiators.

As is apparent from the preceding paragraphs, the anionic polymerization initiator may be the same as, or different from, the alkali metal selected to inactivate active hydrogen compounds and polymerization terminating compounds. For simplicity, the anionic polymerization initiator and the alkali metal are the same. If they are not the same, an additional step, whereby the inactivated compounds and any residual alkali metal are removed before beginning polymerization of 1,3-pentadiene, may have to be added.

The organo-alkali metal compound is suitably selected from the group consisting of organo-lithium compounds, organo-sodium compounds and organo-potassium compounds. The organo-portion of the organo-alkali metal compound is suitably selected from the group consisting of alkyl radicals having from one to ten carbon atoms per alkyl group, alkylaryl radicals having only one alkyl substituent and from 7 to 12 carbon atoms per alkylaryl group, and aryl radicals selected from the group consisting of phenyl, biphenyl, naphthyl and fluorenyl radicals. The organo-portion is beneficially an alkyl radical having from one to six carbon atoms per radical.

The organo-alkali metal compound is desirably an organo-lithium compound selected from the group consisting of isopropyllithium, n-butyllithium, t-butyllithium, sec-butyllithium, t-octyllithium, n-decyllithium, phenyllithium, naphthyllithium, 4-butylphenyllithium, p-tolyllithium, 4-phenylbutyllithium, cyclohexyllithium, 4-butyl-cyclohexyllithium, 4-cyclohexyl-butyllithium, and the like. The organo-alkali metal compound is desirably n-butyllithium.

Finely divided dispersions of an alkali metal in an aliphatic hydrocarbon which does not interfere with the polymerization of 1,3-pentadiene may be used as a polymerization initiator. The aliphatic hydrocarbon is beneficially selected from the group consisting of non-reactive medium and high boiling hydrocarbons up to and including petrolatum. Desirably, the aliphatic hydrocarbon is selected from the group consisting of mineral oils having boiling points within the range of from about 110° to about 400° Centigrade, unsaturated polypiperylene and hydrogenated polypiperylene.

The alkali metal which is dispersed in an aliphatic hydrocarbon is suitably selected from the group hereinbefore listed. Beneficially, the alkali metal is sodium.

One point must be remembered when selecting an aliphatic hydrocarbon. That is, one is adding, when the aliphatic hydrocarbon of choice is a mineral oil, a material, namely the aliphatic hydrocarbon, which may later have to be separated from the polymer of 1,3-pentadiene. Separation is unnecessary when the aliphatic hydrocarbon is either an unsaturated polypiperylene or a hydrogenated polypiperylene.

Chain transfer agents have been used in other anionic polymerization processes for the purpose of preparing polymers having lower molecular weights than polymers similarly prepared without the use of a chain transfer agent is known. See, A. L. Gatzke, "Chain Transfer in Anionic Polymerization: Determination of Chain-Tranfer Constants by Using Carbon-14-Labeled Chain Transfer Agents", *Journal of Polymer Science,* Part A-1, Vol. 7. pp. 2281–92 (1969). Chain transfer agents may also be used for purposes of the present invention.

Chain transfer agents which may be used in conjunction with an alkali metal dispersion are suitably selected from the group consisting of toluene, cumene, xylene, 1,2,3-trimethylbenzene, 1,2,4-trimethylbenzene, 1,3,5-trimethylbenzene, 1,2,3,5-tetramethylbenzene, diisopropylbenzene, diphenyl methane, triphenyl methane and the like. Beneficially, the chain transfer agent is toluene.

When a chain transfer agent is used in conjunction with an alkali metal dispersion, the chain transfer agent is suitably present in an amount of from about 10 to about 150 mole percent, beneficially from about 70 to about 90 mole percent based on amount of 1,3-pentadiene.

The anionic polymerization initiator is used in an amount which may vary over a wide range. Generally the amount will be from about 0.01 to about 25.0 mole percent based on the amount of piperylene (1,3-pentadiene) in the mixture of saturated and unsaturated hydrocarbon molecules. Beneficially, the amount of initiator is from about 0.1 to about 20.0 mole percent based upon the amount of piperylene. Desirably, the amount of initiator is from about 1.0 to about 5.0 mole percent based upon the amount of piperylene.

An upper limit upon the amount of anionic polymerization initiator depends upon factors such as molecular weight desired and cost of the initiator. Conversely, a lower limit upon the level of initiator depends upon factors such as molecular weight desired and the polymerization rate desired.

At very low initiator levels, reaction times may become excessively long and may result in poor polymer yields because of chain termination reactions. Initiator amounts are, as a general rule, inversely related to polymer molecular weight. That is, a large amount of initiator results in a low molecular weight polymer and vice versa.

Anionic polymerization initiators which are insoluble in a reaction mixture must be dispersed throughout the reaction mixture by an agitation means in order to obtain maximum polymer yield from said initiator. It has been found that the amount of insoluble initiator required to produce a given polymer yield is, all other variables being held constant, inversely proportional to the rate of agitation of said agitation means. That is, a high level of initiator is needed when using a low rate of agitation whereas a low level of initiator is needed when using a high rate of agitation.

Anionic polymerization initiators which are soluble in the reaction mixture need not, as hereinbefore noted, be dispersed by an agitation means. That is not to say, however, that an agitation means may not be used in conjunction with a soluble initiator. Agitation may be required for other purposes, such as cooling of the reaction mixture.

It has been found that large amounts of cyclopentadiene will interfere with polymerization of 1,3-pentadiene. Small amounts of cyclopentadiene are, however, tolerable when a low molecular weight, low viscosity polymer is desired. It has also been found that molecular weight distribution of the polymer of 1,3-pentadiene increases in breadth as the amount of cyclopentadiene increases. A discernible increase in breadth is achieved when polymerization stocks contain more than about one percent by weight of cyclopentadiene.

The inert atmosphere suitably comprises a gaseous element or compound which is chemically unreactive, within detectable limits, with components of the polymerization feedstream, with polymerization products derived therefrom or with the polymerization initiator. The gaseous element is beneficially selected from the group consisting of helium, neon, argon and nitrogen. Nitrogen, because of cost considerations and availability, is the gaseous element of choice when using one of the hereinabove identified polymerization initiators other than metallic lithium.

Reaction time may vary from less than about one hour to more than about 100 hours. Actual reaction time depends upon a number of polymerization parameters, e.g., level of initiator, temperature, rate of agitation, dispersion of initiator, and pressure. Reaction time is beneficially from about 0.08 to about 25 hours, desirably from about 0.5 to about 2 hours.

Pressure is not particularly critical. In fact, autogenous pressure is generally suitable for polymerization in accordance with the present invention. Pressures greater than autogenous pressure may be employed, but are generally not necessary.

Temperatures suitable for polymerization in accordance with the present invention will vary with the anionic polymerization initiator and with desired rate of polymerization.

Anionic polymerization initiators suitable for use with the present invention are set forth hereinabove. The initiators are available in a variety of physical forms. Alkali metals suitable for use with the present invention are normally solid at 25° Centigrade. Alkali metal alloys are available, depending upon composition thereof, either as normally solid materials or as liquid materials at 25° Centigrade. An alkali metal dispersion is a suspension of a finely divided, normally solid alkali metal in an aliphatic hydrocarbon. The aliphatic hydrocarbons vary in consistency from an oil to a waxy amorphous material at 25° Centigrade. Organo-alkali metal compounds are generally available as solutions in a liquid hydrocarbon. The solutions are generally liquid at 25° Centigrade.

As a general rule, polymerization rates will increase as polymerization temperature increases with each of the aforementioned anionic polymerization initiators.

It has been found that polymerization rates increase dramatically when a normally solid alkali metal or alkali metal alloy is melted and dispersed throughout a reaction mixture. Potassium is an alkali metal which has a melting point of 63° Centigrade. A polymerization of piperylene concentrate at a temperature of 45° Centigrade using pieces of metallic potassium as the initiator resulted in a 48 percent conversion of 1,3-pentadiene monomer to polymer after 3 hours and an 82 percent conversion after 6 hours. By way of comparison repeating the polymerization at a temperature of 70° Centigrade resulted in a nearly 100 percent conversion after three minutes.

When using metallic potassium as the initiator, the polymerization temperature is desirably from about 63° to about 190° Centigrade, preferably from about 63° to about 70° Centigrade. Temperatures of from about 70° Centigrade to 190° Centigrade and higher may be employed, but are not necessary.

The anionic polymerization initiators suitable for use with the present invention will also inactivate active hydrogen compounds and polymerization terminating compounds. As a general rule, inactivation of such compounds proceeds at a faster rate than polymerization of 1,3-pentadiene.

It has been found that with certain initiators most, if not all, of such compounds may be inactivated at a first temperature where polymerization of 1,3-pentadiene proceeds very slowly. After inactivation of at least 50 percent, desirably at least 80 percent and preferably at least 90 percent of the active hydrogen compounds and polymerization terminating compounds contained in a reaction mixture, the reaction mixture may be heated to a second temperature. The second temperature is that temperature at which a satisfactory rate of polymerization of 1,3-pentadiene is obtained.

The "certain initiators" are selected from the group consisting of metallic sodium and organo-alkali metal compounds. The organo-alkali metal compounds are set forth hereinabove.

When using metallic sodium, the first temperature is desirably from about 96° to 100° Centigrade. The first temperature must be sufficiently high to melt the metallic sodium. If the first temperature is greater than about 100° Centigrade, polymerization of 1,3-pentadiene will commence before inactivation of more than about 90 percent of the active hydrogen compounds and polymerization terminating compounds.

When using metallic sodium, the second temperature is desirably from about 110° to about 190° Centigrade and preferably from about 120° to about 170° Centigrade. At temperatures below about 110° Centigrade, polymerization of 1,3-pentadiene, if it occurs, will proceed very slowly. Temperatures in excess of 190° Centigrade will effectively polymerize 1,3-pentadiene but are believed to be uneconomical.

When the anionic polymerization initiator is a soluble organo-alkali metal compound, inactivation of polymerization terminating compounds and active hydrogen compounds contained in a starting material will occur at room temperature. Accordingly, the first temperature is beneficially from about 15° to about 75° Centigrade, preferably from about 20° to about 35° Centigrade.

It has been found that when the initiator is an organo-alkali metal compound, particularly when it is n-butyllithium, the second temperature is greater than about 80° Centigrade. With n-butyllithium as the initiator, the second temperature is preferably from about 90° to about 120° Centigrade.

Temperatures for other anionic polymerization initiators useful in the present invention are readily determined without undue experimentation.

When polymerization is generally complete, the polymerization initiator is inactivated by adding an external chain-terminating agent. The polymer is then separated, washed and dried using conventional recovery techniques.

External chain-terminating agents which can be added to the anionic polymerization system of this invention are similar to those which have been used in terminating other anionic polymerization reactions. Several external chain-terminating agents are listed by Szwarc in U.S. Pat. No. 3,070,579, the teachings of which are incorporated herein by reference thereto. Among those which are highly useful are:

(1) carbon dioxide, which, when followed by acidification, produces the carboxyl group (—COOH);
(2) carbon bisulfide, which, when followed by acidification, produces the carbodithiol group (—CSSH);
(3) ethylene oxide which, when followed by acidification, produces the hydroxyethyl group (—CH$_2$—CH$_2$OH); and
(4) proton donors such as water, alcohols, or acids which donate a hydrogen atom.

This invention is not limited to a particular external terminating agent. Suitable external terminating agents include water; methyl alcohol; carbon dioxide; lower alkylene oxides, e.g., ethylene oxide, propylene oxide and butylene oxide; ethylene sulfide; propylene sulfide; butylene sulfide; carbon disulfide; epichlorohydrin; lower alkyl aldehydes, e.g., formaldehyde, acetaldehyde, propionaldehyde, and butylaldehyde; and lower alkyl ketones, e.g., acetone, methyl ethyl ketone, diethyl ketone, and dibutyl ketone. As used herein the terms "lower alkyl" and "lower alkylene" respectively mean those alkyl and alkylene groups having 1–4 carbon atoms.

It is generally desirable to neutralize externally terminated polymers prior to polymer recovery. This can be accomplished by using a neutralizing acid. Illustrative neutralizing acids are anhydrous hydrochloric acid, acetic acid, anhydrous phosphoric acid, pyrophosphoric acid, toluene sulfonic acid and water.

Selections of a suitable nuetralizing acid is governed in part by the fact that an externally terminated polymer is a conjugate base of an acid. A conjugate base may be neutralized by any acid which is more acidic than the conjugate acid of the conjugate base.

Polymers of piperylene prepared in accordance with the present invention are composed of the three constitutional repeating units (CRU) set forth below:

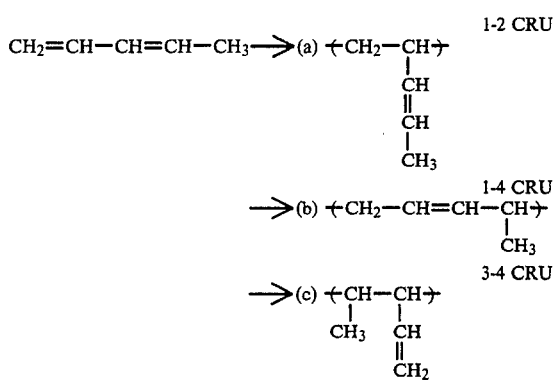

After hydrogenation, the 1-2 CRU yields a pendant propyl group, the 1-4 CRU a pendant methyl group and the 3-4 CRU a pendant methyl group and a pendant ethyl group. In addition, when a monofunctional organo-alkali metal initiator is used, the organo portion of the initiator is attached to one end of a molecule of polypiperylene. The molecule of polypiperylene also has a second end. After termination with an external terminating agent, the second end will have an external terminating agent functionality attached thereto. When a chain transfer agent is used, at least some of the polymer molecules will have one end terminated by the chain transfer agent.

The polymers of piperylene prepared in accordance with the present invention are believed to be branched and generally devoid of any crosslinking or cyclization.

Initiator selection has been found to have a marked effect upon amounts of dimers, trimers and tetramers of 1,3-pentadiene produced during polymerization of piperylene in accordance with the present invention. When using a soluble organo-alkali metal initiator, such as n-butyllithium, no more than trace amounts of said dimers, trimers and tetramers are produced.

When using anionic polymerization initiators other than organo-alkali metal compounds, varying amounts of said dimers, trimers and tetramers are produced. When using metallic sodium, amounts of said dimers, trimers and tetramers are, based upon weight of polymer, respectively about 17 weight percent, about 9 weight percent and about 3 weight percent. When using metallic potassium, amounts of dimers, trimers and tetramers are about one-half those produced when using metallic sodium as the anionic polymerization initiator.

The amounts of dimers, trimers and tetramers set forth in the preceding paragraphs are based upon an assumption that polymerization is allowed to proceed to completion. Persons skilled in the art will understand that amounts of dimers and the like may be increased by a number of techniques. One technique is to terminate polymerization prior to completion.

Polymer viscosity will vary inversely with amounts of dimers, trimers and tetramers of 1,3-pentadiene produced during polymerization of piperylene in accordance with the present invention. Accordingly, when using n-butyllithium as the anionic polymerization initiator, polymer viscosity will be higher than when using metallic sodium as the initiator.

It has surprisingly been found that the process of the present invention is not a typical anionic polymerization process. In a typical anionic polymerization process, a supply of monomer is required for continued polymer chain growth. In other words, no further reaction takes place once the supply of monomer is depleted. In the process of the present invention, a detectable amount of reaction takes place after the supply of 1,3-pentadiene monomer has been depleted.

In the process of the present invention, it has been found, by gas chromatograph analysis, that amounts of dimers and trimers of 1,3-pentadiene in the reaction mixture are maximized when there is no longer any 1,3-pentadiene monomer to be polymerized. If the reaction mixture is maintained under reaction conditions at the second temperature for an additional length of time, the amounts of dimers and trimers of 1,3-pentadiene will decrease to a certain point, after which no further decrease is observed. At that point, amounts of dimers and trimers of 1,3-pentadiene will be about one-half of the aforementioned maximized amounts.

A reduction in the amounts of dimers and trimers of pentadiene is more noticeable when the polymerization initiator is metallic sodium than when the polymerization initiator is a soluble organo-alkali metal compound. As noted hereinbefore, no more than trace amounts of dimers and trimers are produced with n-butyllithium whereas 17 weight percent dimers and 9 weight percent trimers are produced with metallic sodium.

Polymers of piperylene prepared in accordance with the present invention have certain characteristic ratios of constitutional repeating units depending upon the initiator selected.

When the initiator is metallic sodium, the amounts of constitutional repeating units, as determined by carbon-13 Nuclear Magnetic Resonance analysis and based on total amount of constitutional repeating units is:
1-2 CRU—from about 54 to about 67 percent
3-4 CRU—from about 4 to about 14 percent
1-4 CRU—from about 23 to about 40 percent
Beneficially the ratio of constitutional repeating units is:
1-2 CRU—from about 57 to about 66 percent
3-4 CRU—from about 5 to about 13 percent
1-4 CRU—from about 22 to about 38 percent
Desirably the ratio of constitutional repeating units is:
1-2 CRU—from about 59 to about 63 percent
3-4 CRU—from about 5 to about 10 percent
1-4 CRU—from about 26 to about 37 percent.

When the initiator is metallic potassium, the amounts of constitutional repeating units, as determined by carbon-13 nuclear magnetic resonance analysis and based on total amount of constitutional repeating units is:
1-2 CRU—from about 43 to about 53 percent
3-4 CRU—from about 8 to about 16 percent
1-4 CRU—from about 35 to about 45 percent
The ratio of constitutional repeating units is beneficially:
1-2 CRU—from about 44 to about 52 percent
3-4 CRU—from about 9 to about 15 percent
1-4 CRU—from about 36 to about 44 percent
The ratio of constitutional repeating units is desirably:
1-2 CRU—from about 46 to about 50 percent
3-4 CRU—from about 10 to about 14 percent
1-4 CRU—from about 38 to about 42 percent When the initiator is metallic lithium, the amounts of constitutional repeating units, as determined by carbon-13 Nuclear Magnetic Resonance analysis and based on total amount of constitutional repeating units is:
1-2 CRU—from about 33 to about 43 percent
3-4 CRU—from about 0.1 to about 7 percent
1-4 CRU—from about 54 to about 64 percent
Beneficially the ratio of constitutional repeating units is:
1-2 CRU—from about 34 to about 42 percent
3-4 CRU—from about 0.5 to about 6 percent
1-4 CRU—from about 55 to about 63 percent
Desirably the ratio of constitutional repeating units is:
1-2 CRU—from about 36 to about 40 percent
3-4 CRU—from about 1 to about 5 percent
1-4 CRU—from about 57 to about 61 percent When the initiator is an organo-lithium compound such as n-butyllithium, the amounts of constitutional repeating units, as determined by carbon-13 Nuclear Magnetic Resonance analysis and based on total amount of constitutional repeating units is:
1-2 CRU—from about 37 to about 47 percent
3-4 CRU—from about 0.1 to about 6 percent
1-4 CRU—from about 50 to about 61 percent
Beneficially the ratio of constitutional repeating units is:
1-2 CRU—from about 38 to about 46 percent
3-4 CRU—from about 0.5 to about 5 percent
1-4 CRU—from about 52 to about 60 percent
Desirably the ratio of constitutional repeating units is:
1-2 CRU—from about 40 to about 44 percent
3-4 CRU—from about 1 to about 4 percent
1-4 CRU—from about 54 to about 58 percent It is believed that as the 1-2 constitutional repeating unit content of piperylene polymers increases, kinematic viscosity of the polymer decreases. One method of determining kinematic viscosity involves use of a Cannon Ubbelohde viscometer.

Polypiperylene may be functionalized or further treated in accordance with a number of known processes to produce useful products. Illustrative further treatments include hydrogenation, phenolation, epoxidation, hydroxylation, halogenation, sulfonation, addition of maleic anhydride and the like.

The polymers of 1,3-pentadiene, or piperylene, prepared in accordance with the present invention may be hydrogenated using conventional technology. Illustrative procedures are discussed by C. W. Moberly in *The Encyclopedia of Polymer Science Technology* (1967) at pages 557-68. Also of interest are the hydrogenation procedures disclosed in U.S. Pat. Nos. 4,101,599 and 4,122,023, the teachings of which are incorporated herein by reference thereto.

Hydrogenation of liquid polypiperylene is carried out in the presence of a hydrogenation catalyst. Hydrogenation parameters include time, temperature and gaseous hydrogen pressure. Time is suitably from about 0.5 to about 100 hours, preferably from about 1 to about 4 hours. Temperature is suitably from about 0° Centigrade to about 250° Centigrade, preferably from about 30° Centigrade to about 150° Centigrade. Gaseous hydrogen pressure is suitably from about 10 to about 2,000 pounds per square inch gauge, preferably from about 50 to about 150 pounds per square inch gauge.

Hydrogenation may be carried out in the presence or absence of a diluent such as an inert solvent. A diluent is not necessary if the liquid polypiperylene has a viscosity which is sufficiently low. By "sufficiently low", it is meant that the hydrogenation catalyst can be dispersed throughout the liquid polypiperylene with stirring. By way of illustration only, a polymer having a viscosity of 2,000,000 centistokes at 67° Farenheit must be diluted.

Suitable inert solvents are selected from the group consisting of ketones, e.g., methyl ethyl ketone; aliphatic hydrocarbons, e.g., heptane, hexane, pentane or cyclohexane or mixtures thereof; and aromatic hydrocarbons, e.g., toluene. The inert solvent is beneficially an aliphatic hydrocarbon solvent.

If there is no interest in recovering unreacted portions of the mixture of saturated and unsaturated hydrocarbons for other uses, hydrogenation of liquid polypiperylene may be carried out in the presence of said unreacted portions rather than in the presence of an inert aliphatic hydrocarbon solvent. Hydrogen usage increases when using unreacted portions of the mixture of saturated and unsaturated hydrocarbons as a diluent rather than an inert solvent. While this is a disadvantage, it is offset by eliminating steps such as addition and removal of the inert solvent.

Hydrogenation catalysts used to hydrogenate other unsaturated polymers are also useful for purposes of the present invention. Hydrogenation catalysts generally fall into the categories (a) metal and supported metal catalysts, (b) noble metal and supported noble metal catalysts and (c) organometal-metal salt combinations, also referred to as homogeneous or soluble catalysts.

Illustrative metal and supported metal catalysts include unsupported nickel, Raney nickel, Rufert nickel, nickel-kieselguhr, nickel-alumina and nickel on diatomaceous earth. Illustrative noble metal and supported noble metal catalysts include palladium, platinum, rhodium, ruthenium, and palladium on carbon.

Illustrative organometal-metal salt combinations include triisobutylaluminum in combination with acetylacetonates of cobalt, chromium, or tetraisopropyl titanate; amine boranes, and chromium or tin tetraalkylboron compounds.

The hydrogenation catalyst is preferably a palladium on carbon support catalyst.

In a batch hydrogenation, the hydrogenation catalyst is suitably employed in an amount of from about 0.1 to about 50 weight percent based on weight of polypiperylene. The hydrogenation catalyst is beneficially employed in an amount of about 5 weight percent based on weight of polypiperylene. Operating outside the aforementioned limits is believed to be economically impractical. A continuous hydrogenation may also be practiced.

After completion of the hydrogenation, the hydrogenation catalyst and the diluent are removed from the reaction mixture by conventional methods. A suitable method includes filtration followed by flash distillation.

The hydrogenated polymers of 1,3-pentadiene produced in accordance with the present invention have a large number of uses. The hydrogenated polymers may be used as (a) lubricant basestocks; (b) fully formulated synthetic lubricants; (c) a component in a blend with esters, oils, synthetic hydrocarbons, phosphate esters and polyoxyalkylene glycols; (d) a viscosity index improver (e) hydraulic fluids; (f) heat transfer fluids; (g) transformer fluids; (h) plasticizers; and (i) cling additives for polymeric film.

Lubricant basestocks and fully formulated synthetic lubricants use hydrogenated polypiperylenes either alone or in admixture with other fluids such as polyalkylene glycols, poly-α-olefins, pentaerythritol esters, dicarboxylic acid esters, esters derived from alcohols with 1-8 hydroxyl groups, phosphate esters, polyphenyls, hydrogenated polydienes, silicones and mineral oils. The basestocks and formulated lubricants may also contain inhibitors and other additives which do not detract from desired properties.

Illustrative end use applications for lubricants containing the hydrogenated polypiperylenes of the present invention include use as lubricants for compression and spark ignition engines, two cycle engines, rotary engines, gas engines, gas turbine engines, and aircraft and industrial equipment such as pumps and compressors.

The following examples illustrate the manner in which the principles of the present invention are applied. The examples are not to be construed as limiting the scope of the invention. All parts and percentages are by weight and all temperatures are in degrees Centigrade unless otherwise specified.

DESCRIPTION OF POLYMERIZATION APPARATUS

A. 300 Milliliter and 600 Milliliter Polymerization Apparatus

1. Description: A polymerization apparatus was assembled comprising a 300 milliliter stainless steel high pressure reaction vessel, commercially available from Autoclave Engineers, equipped with a pulley-driven 1400-revolutions-per-minute stirrer, a cooling loop, a pressure transducer, a first inlet line, a second inlet line, a thermowell, and a frangible assembly with a rupture disk rated for 1000 pounds per square inch gauge. The frangible assembly was connected by a separate line to a blowdown tank which was constantly purged with gaseous nitrogen and vented to the atmosphere. The cooling loop was connected to a cooling water supply line. The pressure transducer was connected to a pressure recorder. A single thermocouple was inserted into the thermowell and connected to a temperature recorder.

The first inlet line had a first end connected to the reaction vessel, a second end remote from the first end and a ball valve, the ball valve being located between the first and the second end. A septum adapter was fitted onto the second end of the first inlet line. A rubber septum was fitted over the septum adapter.

The second inlet line had a first end connected to the reaction vessel, a second end remote from the first end and a high pressure valve, the high pressure valve being located between the first end and the second end. A septum adapter was fitted over the second end of the second inlet line. The second inlet line was connected to a dual purpose line by way of the septum adapter fitted over the second end of the second inlet line.

The dual purpose line had a first end connected to the second end of the second inlet line and a second end connected to a vacuum pump. A three-way valve and a T-connection were interposed between the first and the second end of the dual purpose line with the T-connection being between the first end of the dual purpose line and the three-way valve.

The T-connection consisted of a hollow vertical stem having a first end and a second end remote from the first end. The second end of the vertical stem was connected to a hollow horizontal tube at a point midway between a first end and a second end thereof. The first and second ends of the hollow horizontal tube were connected to the dual purpose line. The first end of the vertical stem was connected by a line to a nitrogen source.

The three-way valve was connected, by way of the dual purpose line, to the reaction vessel and to a vacuum pump, and, by way of a connecting line, to a dual chamber bubbler.

The dual chamber bubbler had a first, or upper, chamber and a second, or lower, chamber. A hollow tube extending from the first chamber and for a distance into the second chamber connected the chambers. The hollow tube had a first end connected to the first chamber and a second end remote from the first end. The first chamber also had incorporated therein an inlet connection to which the connecting line was connected.

The first chamber also had incorporated therein an inlet connection to which the connecting line was connected.

The second chamber had a first end proximate to the first chamber and a second end remote from the first end. The second end of the hollow tube was proximate to, but spaced apart from, the second end of the second chamber.

The second chamber had incorporated therein a vent to the atmosphere, the vent being located proximate to the first end of the second chamber and remote from the second end of the hollow tube. The second chamber was filled with an amount of mineral oil sufficient to cover the second end of the hollow tube yet leave the vent clear of mineral oil.

The 600-milliliter apparatus differed from the 300-milliliter apparatus in two aspects. First, a 600-milliliter stainless steel high pressure reaction vessel commercially available from Parr Instrument Company was used rather than the aforementioned 300-milliliter vessel. Second, rather than using a single thermocouple, eight thermocouples were inserted into the thermowell and connected to a 16 point recording apparatus commercially available from Honeywell, Inc. under the trade designation Honeywell Electronik-15.

2. Evacuation, Purging and Establishing a Nitrogen Atmosphere: The apparatus was evacuated by (a) turning the three-way valve so that the bubbler was disconnected and the vacuum pump and apparatus were connected; (b) turning off the nitrogen source; and (c) placing the inside of the apparatus under a reduced (subatmospheric) pressure. The apparatus was purged with nitrogen by (a) clamping the dual purpose line between the vacuum pump and the three-way valve; and (b) turning on the nitrogen source. The apparatus was evacuated, then purged, then evacuated a second time and finally purged a second time. After the second nitrogen purge, the three-way valve was turned so that the vacuum pump was disconnected and the bubbler and apparatus were connected.

B. 1-Liter and 2-Liter Polymerization Apparatus

1. Description: A 2-liter polymerization apparatus was assembled and connected in the same manner as the 300-milliliter apparatus. The 2-liter apparatus differed from the 300-milliliter apparatus only in the following respects: (a) the reaction vessel was a 2-liter stainless steel high pressure reaction vessel commercially available from Parr Instrument Company rather than a 300-milliliter vessel; and (b) a pulley driven dual blade variable speed (425 to 800 revolutions per minute) stirrer was used rather than a 1400-revolutions-per-minute stirrer. The 1-liter apparatus differed from the 2-liter apparatus only in the size of the reaction vessel.

2. Evacuation, Purging and Establishing a Nitrogen Atmosphere: The process hereinbefore described with respect to the 300-milliliter polymerization apparatus was also used to establish a nitrogen atmosphere in the 1-liter and 2-liter polymerization apparatus.

C. 10 Gallon Polymerization Apparatus

A 10-gallon jacketed 316 stainless steel reactor vessel rated for a working pressure of 750 pounds per square inch gauge, equipped with an agitator, a thermowell, a pressure transducer, a sample line and a 750 pounds per square inch gauge frangible assembly, and having an upper end and a lower end was used as a polymerization apparatus. The reactor vessel was commercially available from Bench Scale Equipment Company.

Heating and cooling of the reactor vessel was accomplished by circulating heat transfer fluid through its jacket.

The lower end of the reactor vessel had a discharge port. The upper end of the reactor vessel had a first inlet port which was used for adding solid material to the reactor vessel, a second inlet port which was used for adding liquid and gaseous materials to the reactor vessel, and a third inlet port for adding molten or liquid initiator materials to the reactor vessel.

An angularly disposed downwardly sloping multiple port inlet manifold having a lower end in communication with a vertical conduit, which in turn was operatively connected to the second inlet port of the reactor vessel, was used to add all reactants except for the polymerization feedstream (piperylene concentrate) and acid to the reactor vessel.

A first separate angularly disposed downwardly sloping inlet line having a lower end in communication with the vertical conduit at a location between the lower end of the multiple port inlet manifold and the second inlet port of the reactor vessel was used to add the polymerization feedstream to the reactor vessel. The first separate inlet line had incorporated therein a weighing tank from which piperylene concentrate could be added to the reactor vessel by nitrogen pressure.

A second separate angularly disposed downwardly sloping inlet line having a lower end in communication with the vertical conduit at a location between the lower end of the multiple port inlet manifold and the second inlet port of the reactor vessel was used to add acid to the reactor vessel.

The multiple port inlet manifold had a first port connected to a gaseous nitrogen source, a second port connected to a vacuum pump system and a third port connected to a line purged with gaseous nitrogen and vented to the atmopshere.

Addition of material to the reactor vessel is suitably mechanized or automated using known equipment in a manner familiar to the skilled artisan.

2. Evacuation, Purging and Establishing a Gaseous Nitrogen Atmophere: The apparatus was evacuated and purged a number of times before a gaseous nitrogen atmosphere was established. The apparatus was evacuated by opening only the second port of the multiple port inlet manifold to place the inside of the apparatus under a reduced or subatmospheric pressure.

After the apparatus had been evacuated for a suitable length of time, the second port (connected to a vacuum pump system) was closed and the first port of the multiple port inlet manifold which was connected to a gaseous nitrogen source was opened. The reactor vessel was pressurized with nitrogen to about 60 pounds per square inch gauge.

The first port (gaseous nitrogen source) was then closed and the third port of the multiple port inlet manifold was opened. After the reactor vessel had a pressure equal to atmospheric pressure, the third port was closed.

The cycle of evacuation, purging and venting was repeated until there is a reasonable degree of assurance that a gaseous nitrogen atomsphere was established.

Reducing the Amount of Cyclopentadiene in a Piperylene Concentrate

The 10-gallon polymerization apparatus was used to reduce the amount of cyclopentadiene contained in an amount of piperylene concentrate.

An amount (0.42 kilograms) of sodium metal which had been previously cut into small pieces and covered with mineral oil was added to the apparatus through first inlet port at the upper end of the reactor vessel while the reactor vessel was being swept with gaseous nitrogen. The first inlet port was then sealed and a nitrogen atmosphere was established as hereinbefore described.

After the nitrogen atmosphere was established, 21.32 kilograms of piperylene concentrate were added to the apparatus through the inlet line from a weighing tank using nitrogen pressure. The piperylene concentrate contained 12.43 kilograms of 1,3-pentadiene and 0.24 kilograms of cyclopentadiene.

The apparatus was then heated to 100° Centigrade and maintained at that temperature for 15 minutes while maintaining the agitator at a rate of 400 revolutions per minute.

The apparatus was then cooled to 85° Centigrade and a sample of the concentrate was removed. Analysis of the sample by capillary gas chromatography showed that 93.2 percent of the cyclopentadiene had reacted whereas no detectable amount of 1,3-pentadiene had reacted.

The apparatus was then cooled to 85° Centigrade after which the second port of the multiple port inlet manifold was opened to evacuate the apparatus. Following flash distillation, a piperylene concentrate having a markedly reduced amount of cyclopentadiene contained therein was recovered (hereinafter referred to as "Purified Piperylene Concentrate").

The procedure hereinabove detailed established that cyclopentadiene reacts much faster than 1,3-pentadiene in the presence of metallic sodium at 100° Centigrade.

EXAMPLE 1

Polymerization of 1,3-Pentadiene from Purified Piperylene Concentrate Using a Metallic Sodium Initiator Pieces of metallic sodium weighing a total of 1.3 grams were placed into the reaction vessel of the 300-milliliter polymerization apparatus hereinbefore described. The reaction vessel was then sealed and a nitrogen atmosphere was established in the manner hereinbefore described.

After the nitrogen atmosphere was established, a 100-milliliter (70-gram) aliquot of purified piperylene concentrate was added by syringe through the rubber septum. The concentrate contained 38.5 grams of 1,3-pentadiene.

The ball valve on the first inlet line and the high pressure valve on the second inlet line were closed after addition of the piperylene concentrate. The stirrer was then actuated and the apparatus and its contents were heated to a temperature of 150° Centigrade.

The temperature was maintained at 150° Centigrade for a period of 90 minutes after which the reaction vessel and its contents were cooled to room temperature.

The reaction vessel was opened after being cooled to room temperature. The reactor contents were then poured into a stainless steel beaker containing 100 milliliters of methanol to inactivate any residual metallic sodium.

Analysis of the contents by capillary gas chromatography showed that more than about 95 percent of the 1,3-pentadiene contained in the piperylene concentrate had polymerized.

Unreacted components of the concentrate and the methanol were removed from the contents using a rotary evaporator at a temperature of 100° Centigrade and at a pressure of about 5 millimeters mercury absolute.

A residue remained after removal of the unreacted components and the methanol. The residue was dissolved in hexane to produce a solution which was filtered to remove solid, particulate material and devolatilized to remove the hexane. Devolatilization was accomplished with a rotary evaporator at a temperature of 100° Centigrade and at a pressure of about 5 millimeters mercury absolute.

Following devolatilization 33 grams of a mobile reddish-brown oil remained. This amounted to an 85.7 percent yield based upon the amount of 1,3-pentadiene in the purified piperylene concentrate.

The reddish-brown oil had a weight average molecular weight (Mw) of 1688 grams per mole, a number average molecular weight (Mn) of 807 grams per mole and a ratio of Mw/Mn of 2.09. Weight average molecular weight and number average molecular weight were determined by gel permeation chromatography.

The ratio of Mw/Mn is a measure of the broadness of distribution of molecular weight.

EXAMPLE 2

Polymerization of 1,3-Pentadiene From Purified Piperylene Concentrate Using A Metallic Lithium Initiator Pieces of metallic lithium weighing a total of 0.37 grams were placed into the reaction vessel of the 300-milliliter polymerization apparatus.

After sealing the reactor vessel and establishing an argon atmosphere in the same manner as used to establish the nitrogen atmosphere in Example 1, 100 milliliters (70.6 grams) of purified piperylene concentrate were added by syringe through the rubber septum. The concentrate contained 38.8 grams of 1,3-pentadiene.

The valves were closed and the stirrer was actuated in the same manner as in Example 1. The apparatus and its contents were then heated, with stirring, to a temperature of 190° Centigrade and maintained at that temperature for a period of 90 minutes after which the apparatus and its contents were cooled to room temperature.

Following addition of 4 milliliters of glacial acetic acid by syringe through the septum, the reactor and its contents were heated to a temperature of 100° Centigrade and maintained at that temperature for 60 minutes.

After cooling to room temperature, the apparatus was opened and a sample of the contents were removed for analysis. Analysis by capillary gas chromatography showed that about 98 percent of the 1,3-pentadiene contained in the purified piperylene concentrate had polymerized.

Following dilution with an excess of tetrahydrofuran and methanol, the contents of the polymerization apparatus were removed from the apparatus and filtered to remove solid, particulate material. The contents, even after dilution, were very viscous and not easily filtered. The diluted contents were then devolatilized as in Example 1 to remove unreacted components, tetrahydrofuran and methanol.

Following devolazilization, about 31 grams of a highly viscous, reddish-brown fluid remained. This amounted to a yield of about 80 percent based upon the amount of 1,3-pentadiene in the purified piperylene concentrate.

The viscous fluid had a weight average molecular weight of 29,310 grams per mole, a number average molecular weight of 5,158 grams per mole and a ratio of Mw/Mn of 5.68.

EXAMPLE 3

Polymerization of 1,3-Pentadiene from Purified Piperylene Concentrate Using a Sodium Hydride Dispersion as the Initiator An amount (2.36 grams) of a 50 percent sodium hydride dispersion in mineral oil was placed in the reactor vessel of the 300-milliliter polymerization apparatus.

After sealing the reactor vessel and establishing a nitrogen atmosphere in the same manner as in Example 1, 102 milliliters (71.4 grams) of purified piperylene concentrate were added to the reactor vessel in the same manner as in Example 1. The concentrate contained 30.85 grams of 1,3-pentadiene.

The apparatus and its contents were heated, with stirring, to a temperature of 170° Centigrade, maintained at that temperature for 120 minutes and then cooled to room temperature.

The apparatus was opened after being cooled to room temperature and a sample of the contents was removed for analysis. Analysis by capillary gas chromatography showed that 38.6 percent of the 1,3-pentadiene contained in the piperylene concentrate had polymerized. The contents were then mixed with a 1:1 weight ratio methanol/tetrahydrofuran solution and devolatilized as in Example 1 to yield 10.41 grams of a mobile reddish-brown oil.

EXAMPLE 4

Polymerization of a Solution of Cis- and Trans-1,3-Pentadiene Using n-Butyllithium Solution as the Initiator After sealing the reactor vessel of the 300-milliliter polymerization apparatus and establishing a nitrogen atmosphere therein as in Example 1, 100 milliliters (72.92 grams) of a 47.91 percent solution of cis- and trans-1,3-pentadiene (34 percent cis- and 66 percent trans-) in cyclohexane and 22.6 milliliters (17.02 grams) of a 15 percent solution of n-butyllithium in hexane were added to the apparatus by syringe through the rubber septum in the order stated. The apparatus and its contents were then heated, with stirring, to a temperature of 170° Centigrade and maintained at that temperature for 90 minutes before cooling to room temperature.

A capillary gas chromatograph analysis of a sample of the contents revealed that all of the cis- and trans-1,3-pentadiene had polymerized.

The contents were first mixed with methanol to inactivate any remaining n-butyllithium, then mixed with glacial acetic acid to acidify, and finally diluted with excess deionized water to yield a dilute mixture. The dilute mixture was extracted four times with hexane to remove polymerized cis- and trans-1,3-pentadiene.

The hexane extracts were combined, filtered to remove solid, particulate material, and devolatilized to yield 35.3 grams of a reddish-brown viscous oil.

EXAMPLE 5

Polymerization of 1,3-Pentadiene from Purified Piperylene Concentrate Using n-Butyllithium in Hexane Solution as the Initiator The 600-milliliter polymerization apparatus was sealed and a nitrogen atmosphere was established therein as in Example 1.

One hundred (100) milliliters (70 grams) of purified piperylene concentrate were added to the apparatus by syringe through the rubber septum. The concentrate contained 33.5 grams of 1,3-pentadiene. About 62.5 milliliters of a 1.6 Molar solution of n-butyllithium in hexane were then added to the apparatus by syringe through the rubber septum.

The apparatus and its contents were heated with stirring, to a temperature of 190° Centigrade and maintained at that temperature for about 1 hour after which the apparatus and its contents were cooled to a temperature of 70° Centigrade.

After being cooled to a temperature between 50° and 70° Centigrade, the apparatus was fitted with a distillation coil. The distillation coil was passed through a cold trap. The apparatus and its contents were then heated to a temperature of 70° Centigrade and maintained at about that temperature to effect removal of unreacted components of the concentrate. A sample of the recovered unreacted components was analyzed using capillary gas chromatography. The analysis did not reveal any detectable amounts of 1,3-pentadiene monomer.

After the analysis of unreacted components, the apparatus was opened and the contents thereof were mixed with methanol to inactivate any remaining n-butyllithium. The mixture of the contents and methanol was then extracted with hexane to remove polymerized 1,3-pentadiene from the mixture.

The hexane containing the polymerized 1,3-pentadiene was then filtered and devolatilized as in Example 1 to yield 32.6 grams of a dark brown oil. This amounted to a 97.3 percent yield based upon the amount of 1,3-pentadiene in the piperylene concentrate.

The dark brown oil had a weight average molecular weight of 1210 grams per mole, a number average molecular weight of 586 grams per mole and a ratio of Mw/Mn of 2.07.

EXAMPLE 6

Polymerization of 1,3-Pentadiene from Purified Piperylene Concentrate Using a Dispersion of Sodium Hydride in Mineral Oil as the Initiator The polymerization apparatus of Example 5 was used in this example. All handling of reactants was conducted inside a dry box having a nitrogen atmosphere established therein.

Before placing purified piperylene concentrate inside the dry box, the concentrate was purged with nitrogen gas. Purging was accomplished by placing purified piperylene concentrate in a narrow graduated cylinder and thereafter bubbling gaseous nitrogen through the concentrate for about 5 minutes. The concentrate was then transferred to a flask into which a flow of gaseous nitrogen had been, and was continuing to be, introduced. After the concentrate was transferred to the flask, the nitrogen flow was stopped and the flask was quickly sealed with a stopper.

An amount (3.3 grams) of a 60 percent dispersion of sodium hydride in mineral oil was mixed with 30 milliliters of hexane to form a hexane/oil solution out of which the sodium hydride was allowed to settle. The hexane/oil solution was then decanted from the sodium hydride. The sodium hydride was then washed into the reactor vessel with 200 milliliters of the nitrogen-purged, treated piperylene concentrate. The piperylene concentrate contained 45 percent by weight (64 grams) 1,3-pentadiene.

The reactor vessel was then sealed and removed from the dry box. The reactor vessel and its contents were heated, with stirring, to a temperature of 190° Centigrade, maintained at that temperature for 2 hours and then cooled to 70° Centigrade.

Removal of unreacted components was accomplished by distillation as in Example 5. Analysis of a sample of the unreacted components as in Example 5 did not reveal any detectable amounts of 1,3-pentadiene monomer.

The reactor vessel was opened after analysis of the unreacted components and 100 milliliters of hexane and 15 milliliters of methanol were added to the contents of the reactor vessel to inactivate residual sodium hydride and to aid in reclaiming polymerized 1,3-pentadiene.

The reactor vessel was reclosed and the contents were stirred for 20 minutes after which the contents were removed from the reactor vessel, filtered and devolatilized as in Example 1 to yield 65.3 grams of an oil. This amounted to a yield of about 100 percent based upon the amount of 1,3-pentadiene in the purified piperylene concentrate.

The oil had a weight average molecular weight of 2138 grams per mole, a number average molecular weight of 372 grams per mole and a ratio of Mw/Mn of 5.74.

EXAMPLE 7

Polymerization of 1,3-Pentadiene from Purified Piperylene Concentrate Using Lithium Aluminum Hydride as the Initiator Using the same polymerization apparatus as in Example 6 and generally the same procedures for handling reactants as in Example 6, polymerization of 1,3-pentadiene from purified piperylene concentrate which had been treated to remove cyclopentadiene was effected with lithium aluminum hydride as the initiator.

Because lithium aluminum hydride was available as a powder, the procedures of Example 6 for recovering sodium hydride from a dispersion in mineral oil were not used. Two hundred milliliters (74.7 grams) of nitrogen-purged, purified piperylene concentrate which had been purged with nitrogen as in Example 6 and 2.5 grams of lithium aluminum hydride were added to the reactor vessel which was then sealed and removed from the dry box.

The reactor vessel and its contents were heated to a temperature of 190° Centigrade, maintained at that temperature for a period of one hour and then cooled to 70° Centigrade for removal and analysis of unreacted components as in Example 6. The analysis showed that 95 percent of the 1,3-pentadiene had polymerized.

After the analysis, the reactor vessel was opened and its contents were transferred to a 1-liter flask containing 300 milliliters of hexane to yield a green solution. About 10 milliliters of methanol was added dropwise to the green solution to inactivate any remaining initiator. The color of the solution changed from green to yellow with the addition of the methanol.

The yellow solution was filtered through a bed of silica, magnesium silicate and diatomaceous earth. The filtrate was devolatilized as in Example 1 to yield 71.5 grams of a golden oil. This amounted to a yield of 95 percent based upon amount of 1,3-pentadiene in the piperylene concentrate.

The golden oil had a weight average molecular weight of 1344, a number average molecular weight of 748 and a ratio of Mw/Mn of 1.8.

EXAMPLE 8

Polymerization of 1,3-Pentadiene from Purified Piperylene Concentrate Using a Metallic Sodium Initiator Pieces of metallic sodium weighing a total of 2.01 grams were placed into the reactor vessel of the one-liter polymerization apparatus hereinbefore described.

After sealing the reactor vessel and establishing a nitrogen atmosphere therein, also as hereinbefore described, 500 milliliters (350 grams) of purified piperylene concentrate were added to the reactor vessel by way of the rubber septum. The concentrate contained 54 percent 1,3-pentadiene (189 grams).

The reactor vessel and its contents were heated to a temperature of 185° Centigrade, maintained at that temperature for a period of 1.5 hours and then cooled to room temperature.

The reactor vessel was opened after being cooled to room temperature and a sample of its contents was removed for analysis by capillary gas chromatography. The analysis showed that 99 percent of the 1,3-pentadiene had polymerized.

About 50 grams of methanol (about 63 milliliters) were then added to the contents of the reactor vessel to inactivate any residual metallic sodium. The contents were then acidified with 4 milliliters of glacial acetic acid, filtered to remove solid, particulate material and devolatilized as in Example 1 to yield 165.3 grams (88 percent of theoretical yield) of a reddish-brown oil.

The reddish-brown oil had a weight average molecular weight of 1287 grams per mole, a number average molecular weight of 527 grams per mole, and a ratio of Mw/Mn of 2.44.

Examples 1 through 8 demonstrate that 1,3-pentadiene is readily polymerized from a purified piperylene concentrate using a variety of anionic polymerization initiators. Examples 1 through 8 also demonstrate that (a) the process is reproducible (Examples 1 and 8) and (b) reactor vessel size is immaterial.

In Examples 9 through 14 and Comparative Example A which follow, the 10-gallon polymerization apparatus described hereinabove was used to polymerize 1,3-pentadiene from a piperylene concentrate which had not been treated to remove cyclopentadiene while varying certain polymerization parameters.

EXAMPLE 9

Polymerization of 1,3-Pentadiene from Piperylene Concentrate Using Metallic Sodium as the Initiator Metallic sodium pieces weighing a total of 0.20 kilograms were loaded into the 10-gallon jacketed reactor vessel through the first inlet port which was then sealed. The reactor vessel was then evacuated and filled with nitrogen twice using the procedure hereinbefore described. Following the second addition of nitrogen, the reactor vessel was evacuated a third time. An amount, 12.01 kilograms, of piperylene concentrate containing 5.693 kilograms of 1,3-pentadiene and 0.215 kilograms of cyclopentadiene was then added to the reactor vessel through the inlet line from a weighing tank using nitrogen pressure.

With the agitator rotating at 400 revolutions per minute, the reactor vessel and its contents were heated to a temperature of 100° Centigrade and maintained at that temperature for a period of 15 minutes. As hereinbefore noted with regard to purification of piperylene concentrate, greater than 93 percent of the cyclopentadiene had reacted after 15 minutes under these conditions.

With the agitator rotating at 250 revolutions per minute, the reactor vessel and its contents were then allowed to rise in temperature to a temperature of 185° Centigrade. The reactor vessel jacket temperature was maintained at about 20° Centigrade above the reactor temperature until a temperature of 185° Centigrade was reached at which time the jacket temperature was equilibrated with the reactor temperature. The rate of the temperature increase was about 1.5° Centigrade per minute.

After 1.5 hours at a temperature of 185° Centigrade, the reactor vessel and its contents were cooled to a temperature of 38° Centigrade. After cooling, 0.570 kilograms of glacial acetic acid were charged into the reactor through the second inlet line from a weighing tank using nitrogen pressure. The reactor vessel and its contents were then heated to a temperature of 110° Centigrade, maintained at that temperature for one hour to inactivate any unreacted sodium, and then cooled to a temperature of 25° Centigrade.

After being cooled to a temperature of 25° Centigrade, the contents of the reactor vessel were drained therefrom via the discharge port and passed through a 2-micron filter bag to remove solid particulate material. Analysis of the filtrate showed a 96.2 percent conversion of 1,3-pentadiene monomer to polymer.

The filtrate was returned to the reactor vessel after the analysis and flashed under a pressure of 8 to 10 pounds per square inch absolute to remove unreacted components and to yield an isolated polymer product. The polymer product was 3.736 kilograms (73 percent of the theoretical yield) of a reddish-brown oil having a Gardner Color of 11. The reddish-brown oil had a weight average molecular weight of 1322 grams per mole, a number average molecular weight of 632 grams per mole, a ratio of Mw/Mn of 2.09 and a viscosity at 210° Fahrenheit of 9 centistokes.

EXAMPLE 10

Duplication of Example 9 Except for an Increased Speed of Agitation and a Reduced Temperature Metallic sodium pieces weighing a total of 0.183 kilograms and 12.25 kilograms of piperylene concentrate containing 6.038 kilograms of 1,3-pentadiene and 0.152 kilograms of cyclopentadiene were added to the 10-gallon reactor vessel and heated at 100° Centigrade with agitation at 400 revolutions per minute for 15 minutes as in Example 9.

After resetting the rate of agitation to 986 revolutions per minute, the reactor vessel and its contents were heated to a temperature of 150° Centigrade at a heating rate of 1.4° Centigrade per minute and maintained at 150° Centigrade for a period of two hours.

Ater the two-hour period, the contents were cooled to a temperature of 38° Centigrade after which 0.53 kilograms of glacial acetic acid were added to the reactor vessel in the same manner as set forth in Example 9.

The contents were further processed in the same manner as set forth in Example 9 to result in an isolated polymer product. Analysis of the filtrate showed a 99 percent conversion of 1,3-pentadiene monomer to polymer.

The polymer product was 5.19 kilograms (86 percent of theoretical yield) of an oil having a Gardner Color of 15, a weight average molecular weight of 1520 grams per mole, a number average molecular weight of 853 grams per mole, a ratio of Mw/Mn of 1.78 and a viscosity at 210° Fahrenheit of 9.8 centistokes.

EXAMPLE 11

Duplication of Example 9 Except for an Increased Speed of Agitation and a Reduced Temperature Metallic sodium pieces having a total weight of 0.183 kilograms and 12.13 kilograms of piperylene concentrate containing 5.98 kilograms of 1,3-pentadiene and 0.151 kilograms of cyclopentadiene were loaded into the reactor vessel as in Example 9 and heated at 100° Centigrade with a speed of agitation of 800 revolutions per minute for 15 minutes.

While maintaining the speed of agitation at 800 revolutions per minute, the reactor vessel and its contents were heated to a temperature of 120° Centigrade at a rate of 2° Centigrade per minute and maintained at that temperature for a period of six hours. A maximum reactor pressure reading of 130 pounds per square inch absolute was recorded during the period of six hours.

After the six-hour period, the contents were cooled to 38° Centigrade and 0.530 kilograms of glacial acetic acid were added thereto in the same manner as set forth in Example 9.

The contents were further processed in the same manner as set forth in Example 9 to result in an isolated polymer product. Analysis of the filtrate showed that no detectable unpolymerized 1,3-pentadiene remained.

The polymer product was 5.313 kilograms (89 percent of theoretical yield) of an oil having a Gardner Color of 12, a weight average molecular weight of 1493 grams per mole, a number average molecular weight of 826 grams per mole, a ratio of Mw/Mn of 1.81 and a viscosity at 210° Fahrenheit of 9.82 centistokes.

EXAMPLE 12

Duplication of Example 9 Except for an Increased Speed of Agitation and Addition of a Soap Metallic sodium chunks having a total weight of 0.203 kilograms and 12.09 kilograms of piperylene concentrate containing 5.728 kilograms of 1,3-pentadiene and 0.226 kilograms of cyclopentadiene were loaded into the reactor vessel as in Example 9. After addition of the piperylene concentrate, 0.0285 kilograms of soap flakes, commercially available from Proctor and Gamble under the trade designation of Ivory Flakes were added to the reactor vessel. The reactor vessel was then sealed and its contents were heated to a temperature of 100° Centigrade with a speed of agitation of 400 revolutions per minute for 15 minutes as in Example 9.

While maintaining the speed of agitation at 400 revolutions per minute, the reactor vessel and its contents were heated to a temperature of 150° Centigrade at a rate of 1.4° Centigrade per minute and maintained at that temperature for a period of two hours. A maximum reactor pressure reading of 182 pounds per square inch absolute was recorded during the two-hour period.

After the two-hour period, the reactor contents were processed as in Example 9 using 0.540 kilograms of glacial acetic acid to yield an isolated polymer product. Analysis showed that 97.6 percent of the 1,3-pentadiene contained in the concentrate had polymerized.

The polymer product was 5.110 kilograms (89 percent of theoretical yield) of an oil having a Gardner Color of 14 and a viscosity at 210° Fahrenheit at 8 centistokes.

EXAMPLE 13

Polymerization of 1,3-Pentadiene from Piperylene Concentrate Using an Alternative Means of Adding a Sodium Metal Initiator A jacketed 2-liter stainless steel addition vessel having an upper end and a lower end and a working pressure rating of 750 pounds per square inch was used to melt sodium metal for addition to the 10-gallon reactor vessel via the third inlet port.

The upper end of the addition vessel had a first inlet port connected to a gaseous nitrogen supply line, a second inlet port connected to a line from a vacuum pump system and a third inlet port fitted with a 1-inch removable cap.

The lower end of the addition vessel had a drain valve connected by a line to the third port at the upper end of the 10-gallon reactor vessel.

The addition vessel was also fitted with a pressure gauge and a pop valve rated at 750 pounds per square inch.

With the bottom valve of the addition vessel closed, a nitrogen atmosphere was established in the addition vessel and in the reactor vessel. The reactor vessel was evacuated and filled with nitrogen as hereinbefore detailed. The addition vessel was evacuated and filled with nitrogen in a similar manner using valves incorporated in the gaseous nitrogen supply line and in the line to the vacuum pump system to alternately evacuate the vessel and then fill it with nitrogen.

While gaseous nitrogen was being added to the addition vessel a second time, the one-inch cap at the upper end of the addition vessel was removed to add 0.3114 kilograms of sodium metal pieces through the third inlet port and then immediately replaced. The valve in the nitrogen supply line was then closed.

The addition vessel and its contents were heated to a temperature of 180° Centigrade to melt the sodium by circulating heated heat transfer fluid through the jacket of the addition vessel.

Meanwhile, the reactor vessel was evacuated a third time after which 12.12 kilograms of piperylene concentrate containing 5.834 kilograms of 1,3-pentadiene and 0.158 kilograms of cyclopentadiene were added in the same manner as in Example 9.

The reactor vessel and its contents were heated to a temperature of 150° Centigrade at a rate of 2° Centigrade per minute with a speed of agitation of 800 revolutions per minute. After the temperature had stabilized at 150° Centigrade for about 5 minutes, the molten sodium was added to the reactor vessel from the addition vessel using a nitrogen pressure of 300 pounds per square inch gauge.

A rise in reactor vessel pressure of 20 pounds per square inch absolute over that which preceded addition of the molten sodium indicated that addition of the molten sodium was generally complete. After a period of about 4 minutes, an increase in temperature to 176° Centigrade and a rise in pressure to 235 pounds per square inch absolute were observed.

Analysis of a sample of the reactor contents taken after the reactor temperature had risen to 176° Centigrade showed that 95 percent of the 1,3-pentadiene had polymerized.

After about 28 minutes, the reactor temperature had cooled to 150° Centigrade. The reactor and its contents were then maintained at that temperature for a period of four and one-half hours.

The reactor vessel and its contents were cooled to a temperature of 38° Centigrade after the four and one-half hour period. After cooling, 0.970 kilograms of glacial acetic acid were charged into the reactor vessel in the same manner as in Example 9. The reactor vessel and its contents were then heated to a temperature of 110° Centigrade, maintained at that temperature for one hour to inactivate any unreacted sodium, and then cooled to a temperature of 25° Centigrade.

After being cooled to a temperature of 25° Centigrade, the contents of the reactor vessel were drained therefrom via the discharge port and passed through a 2-micron filter bag to remove solid particulate material. Analysis of the filtrate disclosed no detectable amounts of 1,3-pentadiene monomer. The filtrate was not further processed, but was saved for hydrogenation.

EXAMPLE 14

Polymerization of 1,3-Pentadiene from Piperylene Concentrate Using Potassium Metal as the Initiator Potassium metal pieces having a total weight of 0.349 kilograms and 12.10 kilograms of piperylene concentrate containing 5.844 kilograms of 1,3-pentadiene and 0.207 kilograms of cyclopentadiene were added to the 10-gallon reactor vessel as in Example 9. The reactor vessel and its contents were heated, as in Example 9, with a speed of agitation of 800 revolutions per minute to a temperature of 70° Centigrade.

A very fast exotherm resulted which caused the reactor vessel and its contents to reach a temperature of 135° Centigrade. Concurrent with the exotherm, an increase in pressure within the reactor vessel to 220 pounds per square inch absolute occurred.

Analysis of a sample of the contents taken at the temperature of 135° Centigrade showed that 96 percent of the 1,3-pentadiene had polymerized.

The reactor vessel and its contents were then cooled to a temperature of 70° Centigrade and maintained at that temperature for a period of 12 hours. The contents were then processed as in Example 13 using 0.520 kilograms of glacial acetic acid to yield a filtrate. Analysis of the filtrate showed that no additional 1,3-pentadiene had polymerized during the 12-hour period.

COMPARATIVE EXAMPLE A

Attempted Polymerization of 1,3-Pentadiene from Purified Piperylene Concentrate Without Using an Anionic Polymerization Initiator The reactor vessel was evacuated and filled with nitrogen twice, in the same manner as in Example 9. The reactor was then evacuated a third time. An amount, 12.27 kilograms, of purified piperylene concentrate containing 47 percent (5.87 kilograms) of 1,3-pentadiene was then added to the reactor vessel as in Example 9.

The reactor vessel and its contents were heated to a temperature of 170° Centigrade at a rate of 1.4° Centigrade per minute. The reactor vessel and its contents were maintained at that temperature for 1.5 hours and then cooled to room temperature.

Capillary gas chromatograph analysis of a sample of the reactor contents showed that only 19 percent of the 1,3-pentadiene monomer present in the piperylene concentrate had been converted. The analysis also showed that only dimers of 1,3-pentadiene had been prepared.

A comparison of Comparative Example A with Examples 1–14 clearly demonstrates that an anionic polymerization initiator is essential and that heat and stirring alone fail to produce a suitable polymer.

A comparison of Examples 9–14 with Examples 1–8 demonstrates that use of a purified piperylene concentrate is not essential. Satisfactory results are also obtained by maintaining the starting material under conditions sufficient to inactivate cyclopentadiene for a certain period of time before starting polymerization of 1,3-pentadiene. The certain period of time is that which is sufficient to inactivate more than 90, preferably more than 98, weight percent of cyclopentadiene contained in the starting material. As hereinabove noted, the starting material may be either a piperylene concentrate or an impure $C_5$ refinery stream. Also as hereinbefore noted, the period of time and the conditions will vary depending upon the initiator of choice.

Examples 9–14 also demonstrate that, while potassium is a suitable initiator, sodium provides greater process latitude through temperature control although at a higher temperature.

Example 12 demonstrates that a lower rate of agitation is suitable provided a soap or surfactant which does not interfere with polymerization of 1,3-pentadiene is present to aid in dispersion of the initiator. Similar results are obtained using other anionic polymerization initiators hereinbefore disclosed. Similar results are also obtained with other piperylene concentrates or impure $C_5$ refinery streams containing varying amounts of 1,3-pentadiene.

Hydrogenation Apparatus

A first hydrogenation apparatus was assembled comprising a 600-milliliter stainless steel high pressure reaction vessel, commercially available from Parr Instrument Company. The reaction vessel was equipped with a stirrer, a cooling loop, a pressure transducer, a hydrogen inlet valve, a vent valve, a thermowell, and a frangible assembly. The frangible assembly had a rupture disk rated for 2000 pounds per square inch gauge.

The vent valve and the frangible assembly were each connected by separate lines to a blowdown tank. The blowdown tank was constantly purged with gaseous nitrogen and vented to the atmosphere.

The hydrogen inlet valve was connected to a gaseous hydrogen supply line. The cooling loop was connected to a cooling water supply line. The pressure transducer was connected to a pressure recorder. Eight thermocouples were inserted into the thermowell. The thermocouples were connected to a 16-point recording apparatus commercially available from Honeywell, Inc. under the trade designation Honeywell Electronik-15.

A second and a third hydrogenation apparatus were also assembled. The second and third apparatus were generally identical to the first hydrogenation apparatus except for reaction vessel capacity and frangible assembly rupture disk rating. The second and third apparatus had a frangible assembly rupture disk rating of 1000 pounds per square inch gauge. The second hydrogenation apparatus had a reaction vessel capacity of 300 milliliters. The third hydrogenation apparatus had a reaction vessel capacity of two liters.

EXAMPLE 15

Hydrogenation of the Polymer of 1,3-Pentadiene Prepared in Example 7

The following ingredients were placed in the first hydrogenation apparatus (600 milliliter capacity) in the order listed to form a reaction mixture: (a) 2.4 grams of hydrogenation catalyst; (b) 132 grams (200 milliliters) of hexane; and (c) 70.4 grams (82.8 milliliters) of the golden oil prepared in Example 7. The catalyst was a carbon-supported palladium hydrogenation catalyst having a palladium content of 5 percent by weight of catalyst.

After addition of the reaction mixture, the hydrogenation apparatus was closed, sealed and pressurized to about 600 pounds per square inch gauge with gaseous hydrogen. The apparatus and its contents were then heated, with stirring, to a temperature of 75° Centigrade and maintained at that temperature for a period of 30 minutes. A pressure reading of 300 pounds per square inch gauge was observed at the end of the 30-minute period.

The apparatus was repressurized to about 600 pounds per square inch gauge with gaseous hydrogen. The apparatus and its contents were then heated to a temperature of 150° Centigrade and maintained at that temperature for a period of two and one-half hours.

The apparatus and its contents were cooled to room temperature (about 25° Centigrade) after the two and one-half hour period. Excess hydrogen was then vented to the atmosphere. The apparatus was unsealed and opened after venting.

The reaction mixture was removed from the hydrogenation apparatus and filtered through a bed of silica gel and diatomaceous earth to remove the catalyst and any particulate matter. The filtrate was first devolatized using a rotary evaporator at a temperature of 70° Centigrade to remove the hexane. Following devolatilization, dimers and trimers were removed from the filtrate by flash distillation. Flash distillation was accomplished at a temperature of 140° Centigrade and at a pressure of about 0.25 millimeters of mercury absolute for a period of 15 minutes.

A yield of 65.8 grams of a colorless oil remained after flash distillation. The oil had a weight average molecular weight of 1481 grams per mole, a number average molecular weight of 844 grams per mole and a ratio of Mw/Mn of 1.75.

Kinematic viscosities of the oil were measured using a Cannon Ubbelohde viscometer. Measured kinematic viscosities were 135.7 centistokes at 100° Fahrenheit and 15.73 centistokes at 210° Fahrenheit. From these kinematic viscosities, a kinematic viscosity at 0° Fahrenheit of 7000 centistokes and a viscosity index of 131 were calculated.

EXAMPLE 16

Hydrogenation of the Polymer of 1,3-Pentadiene Prepared in Example 6

The following ingredients formed a reaction mixture: (a) 2.5 grams of a carbon-supported palladium hydrogenation catalyst having a palladium content of 5 percent by weight of catalyst; (b) 100 milliliters (66 grams) hexane; and (c) 64.3 grams of the oil prepared in Example 6. The reaction mixture was added to the first hydrogenation apparatus in the order listed.

The apparatus was closed, sealed, pressurized with 600 pounds per square inch gauge hydrogen gas, and heated to a temperature of 75° Centigrade. The apparatus and its contents were maintained at that temperature for a period of 30 minutes.

After the pressure had dropped to 300 pounds per square inch gauge, the apparatus was repressurized to 600 pounds per square inch gauge. After repressurization, the apparatus and its contents were heated to a temperature of 150° Centigrade. After 2.5 hours at 150° Centigrade, the apparatus and its contents were cooled to room temperature.

The contents were processed in the same manner as detailed in Example 15 to yield 60.5 grams of a colorless oil. The oil had a weight average molecular weight of 3,479 grams per mole, a number average molecular weight of 450 grams per mole and a ratio of Mw/Mn of 7.73.

EXAMPLE 17

Hydrogenation of the Polymer of 1,3-Pentadiene Prepared in Example 9

The following ingredients formed a reaction mixture (a) 432.24 grams of the polymer of 1,3-pentadiene prepared in Example 9, (b) 500 milliliters (330 grams) of hexane and (c) 15.13 grams of a carbon-supported palladium hydrogenation catalyst having a palladium content of 5 percent by weight of catalyst. The reaction mixture was placed in the reactor vessel of the third hydrogenation apparatus in the order listed.

After addition of the reaction mixture, the reactor vessel was closed, sealed, pressurized with 600 pounds per square inch gauge hydrogen. The pressurized reaction vessel and its contents were heated, with stirring, to a temperature of about 50° Centigrade whereupon an exothermic reaction was observed. The exothermic reaction caused the temperature within the reactor vessel to increase to 150° Centigrade where it was maintained with the aid of the cooling coils.

The temperature of 150° Centigrade and the hydrogen pressure of 600 pounds per square inch gauge were maintained for a period of 6 hours.

After the 6 hours had elapsed, the reactor vessel and its contents were cooled to room temperature. Excess hydrogen was vented from the reaction vessel as in Example 15. The reaction mixture was then removed from the reactor vessel and vacuum filtered through a fine glass-fritted funnel to remove the catalyst. The filtrate was devolatilized in a rotary evaporator at 100° Centigrade and at a pressure of about 1 millimeter mercury absolute to remove the hexane.

After devolatilization, the filtrate was subjected to vacuum distillation at a temperature of 150° Centigrade and at a pressure of about 0.05-0.1 millimeter mercury absolute. Vacuum distillation was continued until no further distillate was collected, a period of about 0.5 hours.

After vacuum distillation, 344 grams of hydrogenated polymer remained. The polymer had a Gardner Color of 3, weight average molecular weight of 1236 grams per mole, a number average molecular weight of 1015 grams per mole and a ratio of Mw/Mn of 1.22. The polymer also had a measured kinematic viscosity at 210° Fahrenheit of 17.20 centistokes. This amounted to an 80 percent recovery based upon amount of unsaturated polymer starting material.

EXAMPLE 18

Hydrogenation of the Filtrate Containing Polymerized 1,3-Pentadiene Prepared in Example 14

The following ingredients formed a first reaction mixture: (a) 13.92 grams of a carbon-supported palladium hydrogenation catalyst having a palladium content of 5 percent by weight of catalyst; and (b) 793.5 grams of the filtrate prepared in Example 14. The reaction mixture was placed in the third hydrogenation apparatus and processed as in Example 17 up to and including devolatilization to yield 353.90 grams of devolatilized filtrate.

A second reaction mixture comprising 11.32 grams of catalyst and 644.66 grams of the filtrate prepared in Example 14 was processed in the same manner as the first reaction mixture. The second reaction mixture yielded 282.85 grams of devolatilized filtrate.

The devolatilzed filtrates from the two reactions were combined and distilled under reduced pressure as in Example 15 to yield 596.54 grams of hydrogenated polymer. By hydrogenated, it is meant that no detectable unsaturation was observed when a sample was analyzed by nuclear magnetic resonance spectroscopy.

The hydrogenated polymer had a Gardner Color of 2 and measured kinematic viscosities of 678 centistokes at 100° Fahrenheit and 47.4 centistokes at 210° Fahrenheit.

EXAMPLE 19

Hydrogenation of the Polymer of 1,3-Pentadiene Prepared in Example 13

The following ingredients formed a reaction mixture: (a) 19.68 grams of a carbon-supported palladium hydrogenation catalyst having a palladium content of 5 percent by weight of catalyst; and (b) 1122.6 grams of the filtrate prepared in Example 13. The reaction mixture was placed in the third hydrogenation apparatus and process as in Example 17 to yield 351.66 grams of hydrogenated polymer.

The hydrogenated polymer had a Gardner Color of 5 and measured kinematic viscosities of 142.08 centistokes at 100° Fahrenheit and 14.4 centistokes at 210° Fahrenheit.

A review of Examples 15-19 demonstrates that hydrogenation of polymerized 1,3-pentadiene prepared as in Examples 1-14 is suitably accomplished either before or after distillation under reduced pressure. Distillation under reduced pressure is used to effect removal of unreacted 1,3-pentadiene monomer as well as dimers, trimers and some tetramers of 1,3-pentadiene.

Hydrogenation before distillation under reduced pressure is advantageous because the unreacted monomer and the dimers and trimers act as a diluent. Thus, the steps of first adding and then removing a nonreactive diluent are omitted. Hydrogenation after distillation under reduced pressure also has advantages notwithstanding the need to add and later remove a nonreactive diluent. One advantage is the ability to recover unsaturated monomers as well as dimers and trimers of 1,3-pentadiene for other uses.

Similar results are obtained with other polymers of 1,3-pentadiene as hereinbefore described.

EXAMPLE 20

Epoxidation of Polymer of 1,3-Pentadiene

A 2-liter round-bottom, three-necked flask having a thermowell was used as an epoxidation apparatus. A mechanical stirrer was fitted into a first neck. A reflux condenser was fitted into a second neck. An addition funnel was fitted into a third neck.

The following ingredients were charged into the epoxidation apparatus through the addition funnel in the order listed to form a reaction mixture: (a) 30.16 grams of 1,3-pentadiene polymer prepared as in Example 9; (b) 100 milliliters of methylene chloride; (c) 25.42 grams of sodium bicarbonate; and (d) 350 milliliters of deionized water.

The reaction mixture was cooled, with stirring, to a temperature of about 5° Centigrade with the aid of an ice bath. A solution of 46.02 grams of 83 percent metachloroperbenzoic acid in 500 milliliters of methylene chloride was then added to the cooled reaction mixture. The solution was added to the cooled reaction mixture over a period of about 1 hour at a rate sufficient to maintain the temperature of the mixture below 10° Centigrade.

After completing addition of the solution, the reaction mixture was stirred for an additional 2.5 hours. The reaction mixture was then allowed to stand and separate into layers, one of which contained methylene chloride. A sample of the methylene chloride layer was removed to determine residual per-acid content by iodometric titration.

Iodometric titration is explained in the analytical procedures section of "Peracid and Peroxide Oxidations" by Sheldon N. Lewis, *Oxidation*, Volumn I, R. L. Augustine, editor, 1969.

The iodometric titration revealed that 99 percent of the per-acid had been converted. The reaction mixture was then transferred to a separating funnel to recover the methylene chloride layer which was predominantly polymer product dissolved in methylene chloride.

The recovered methylene chloride layer was washed three times with 50 milliliter portions of a 10 percent sodium hydroxide solution and once with 300 milliliters of deionized water to convert meta-chlorobenzoic acid, a reaction product, to a water soluble salt. The methylene chloride layer was then dried over anhydrous sodium sulfate and filtered to remove particulate material. The filtrate devolatilized in a rotary evaporator at 100° Centigrade and at a pressure of about 1 millimeter mercury for 60 minutes to yield 32.73 grams of epoxidized resin.

The epoxidized resin had an epoxide content of 0.00401 moles of epoxide per gram of resin (60 percent yield based upon the per-acid used). Epoxide content was determined by the pyridine chloride hydrochlorination method described by J. L. Jungnickel, E. D. Peters, A. Polgar and F. T. Weiss in "Determination of the α-Epoxy Group", *Organic Analysis, Volume I*, Interscience Publishing Company (1953).

The epoxidized resin is useful in conventional epoxy resin applications.

EXAMPLE 21

Phenolation of Polymer of 1,3-Pentadiene

The phenolation procedure used is set forth in "Polypentadiene Modified With Phenols" Japanese Kokai No. 76-92,890.

A 250-milliliter round-bottom, three-necked flask having a thermowell was used as a phenolation apparatus. A mechanical stirrer was fitted into a first neck. A reflux condenser was fitted into a second neck. After a reaction mixture was added to the apparatus, a stopper was inserted into a third neck.

The reaction mixture was a mixture of: (a) 50.35 grams of phenol; (b) 1.58 grams of paratoluenesulfonic acid; (c) 20 grams of toluene; and (d) 51.21 grams of an unsaturated polymer of 1,3-pentadiene prepared as in Example 9.

After addition of the reaction mixture, the apparatus and its contents were heated to a temperature of 100° Centigrade and maintained at that temperature for a period of about 6 hours. The apparatus and its contents were then cooled to a temperature of 80° Centigrade. After cooling, the stopper was removed and 80 milliliters of toluene and 150 milliliters of deionized water were added to the reaction mixture to form a diluted mixture.

The diluted mixture was transferred to a separatory funnel. The dilute mixture was allowed to stand and separate into an aqueous layer and an organic layer. The organic layer was washed with four 50-milliliter portions of deionized water.

A brown solution remained after the washing. The brown solution was devolatilized using a rotary evaporator at 95° Centigrade and at a pressure of about 1 millimeter mercury absolute to yield 79.60 grams of a brown, sticky resinous material which contained some residual phenol.

Analysis of the resinous material by nuclear magnetic resonance spectroscopy showed that about 71 percent of the original unsaturation of the polymer of 1,3-pentadiene had reacted to yield a phenolated polymer of 1,3-pentadiene.

The phenolated polymer of 1,3-pentadiene is useful in conventional synthetic thermosetting resin applications.

EXAMPLE 22

Sulfonation of Polymer of 1,3-Pentadiene

A 250-milliliter round-bottom, three-necked flask having a thermowell was used as a sulfonation apparatus. A mechanical stirrer was fitted into a first neck. A reflux condenser having an upper end and a lower end had the latter fitted into a second neck. An addition funnel was fitted into a third neck. The apparatus was assembled while components thereof were warm having been washed and then dried in an oven.

The upper end of the reflux condenser was fitted with an adapter which in turn was connected to a line which terminated in a water trap. A T-connection was fitted into the line at a point between the adapter at the upper end of the reflux condenser and the water trap.

The T-connection consisted of a hollow vertical stem having a first end and a second end remote from the first end. The second end of the vertical stem was connected to a hollow horizontal tube at a point midway between a first and a second end thereof. The first and second ends of the horizontal tube were connected to the line between the water trap and the reflux condenser. The first end of the vertical stem was connected to a line which in turn was connected to a gaseous nitrogen source.

The gaseous nitrogen source was turned on after the apparatus was assembled and maintained in that configuration until sulfonation was complete.

After assembly, the flask was purged with nitrogen by passing gaseous nitrogen through the apparatus via the addition funnel.

Fifty grams of an unsaturated polymer of 1,3-pentadiene prepared as in Example 9 and 100 milliliters of chloroform were added to the apparatus through the addition funnel to form a mixture.

While gaseous nitrogen was flowing into the addition funnel, 15 milliliters (26.55 grams) of chlorosulfonic acid were added to the mixture to form a reaction mixture. The chlorosulfonic acid was added dropwise over a 20 minute period so that the reaction mixture would remain at a temperature of about 25° Centigrade. An ice bath was also used to maintain the temperature of the reaction mixture at 25° Centigrade.

The reaction mixture reacted during the 20 minute period to liberate, as one reaction product, hydrochloric acid. The ice bath was removed after the 20 minute-period and the reaction mixture was transferred to a 250 milliliter round bottom flask.

The reaction mixture was devolatilized with a rotary evaporator at a temperature of 85° Centigrade and at a pressure of about 1 millimeter mercury absolute to yield a gummy, brown-colored residue weighing 75.87 grams. Analysis of the residue by nuclear magnetic resonance spectroscopy showed that about 84 percent of the original unsaturation had reacted by sulfonation to yield a sulfonated polymer of 1,3-pentadiene.

The sulfonated polymer of 1,3-pentadiene is useful in surfactant formulations.

EXAMPLE 23

Bromination of Polymer of 1,3-Pentadiene

A 500-milliliter round-bottom, three-necked flask having a thermowell was used as bromination apparatus. The necks of the flask were fitted with a mechanical stirrer, a reflux condenser and an addition funnel in the same manner as the 2-liter apparatus of Example 20.

The following ingredients were charged into the flask through the addition funnel to form a mixture: (a) 18.26 grams of an unsaturated polymer of 1,3-pentadiene prepared as in Example 9; and (b) 175 milliliters of chloroform. The addition funnel was then charged with a solution of 56.91 grams of bromine in 150 milliliters of chloroform.

After the flask was wrapped in aluminum foil to block out light, the flask and the mixture contained therein were cooled to a temperature of 0° Centigrade using an ice bath. The bromine solution was then added slowly to the mixture to form a reaction mixture. By slowly, it is meant that the bromine solution was added at a rate sufficient to maintain the reaction mixture at a temperature of no greater than about 2° Centigrade. Addition of the bromine solution was accomplished in 2.5 hours.

After addition of the bromine solution was complete, about 4 grams of sodium metabisulfate was added to the reaction mixture to neutralize any residual bromine. The neutralized reaction mixture was then filtered to remove solid material.

Analysis of the filtrate by nuclear magnetic resonance spectroscopy showed that generally all of the original unsaturation had reacted to yield a brominated polymer of 1,3-pentadiene. After devolatilization of the filtrate using a rotary evaporator as in Example 25, a reddish-brown liquid resin remained.

The brominated polymer of 1,3-pentadiene is useful as a liquid fire retardant additive.

Similar results are obtained with other polymers of 1,3-pentadiene prepared in accordance with the present invention as exemplified in Examples 1–8 and 10–14.

Polymers of 1,3-pentadiene prepared in accordance with this invention may either be hydroxylated or terminated by means of a reactant such as ethylene oxide and carbon dioxide.

Copolymers of 1,3-pentadiene and anionically polymerizable monomers such as isoprene, vinyltoluene, styrene, alpha-methylstyrene and tertiary-butylstyrene are prepared by copolymerizing an anionically polymerizable monomer with a piperylene concentrate. The piperylene concentrate preferably has a reduced cyclopentadiene content. A method for reducing cyclopentadiene content is described hereinabove.

What is claimed is:

1. A method for anionically preparing polymers of 1,3-pentadiene from a distillation cut available as a by-product of crude oil cracking operations, said distillation cut being a mixture of saturated and unsaturated hydrocarbon molecules, at least 50 percent by weight of said molecules having 5-carbon atoms per molecule, said mixture comprising cis-1,3-pentadiene, trans-1,3- pentadiene, cyclopentadiene and other 5-carbon atom molecules, the method comprising:
(a) forming a reaction mixture by contacting, in an inert atmosphere, the mixture of saturated and unsaturated hydrocarbon molecules with an amount of an anionic polymerization initiator, the amount being sufficient to (i) inactivate the chain termination function of generally all cyclopentadiene contained in the mixture and (ii) initiate polymerization of 1,3-pentadiene;
(b) heating the reaction mixture to a first temperature, said first temperature being sufficiently high to cause the cyclopentadiene contained in the reaction mixture to react with the initiator to form a reaction product which does not interfere with polymerization of 1,3-pentadiene and maintaining dispersal of the initiator throughout the reaction mixture for a period of time sufficient to inactivate more than about 90 percent of the cyclopentadiene contained in the reaction mixture; and
(c) subsequent to inactivation of the cyclopentadiene, heating the reaction mixture to a second temperature, the second temperature being sufficiently high to initiate polymerization of 1,3-pentadiene, and maintaining dispersal of the initiator throughout the reaction mixture for a period of time sufficient to attain a desired polymer yield.

2. The method of claim 1 wherein the anionic polymerization initiator is selected from the group consisting of alkali metals, alloys of two or more alkali metals, organo-alkali metal compounds, alkali metal hydrides and alkali metal aluminum hydrides.

3. The method of claim 1 wherein the anionic polymerization initiator is metallic sodium.

4. The method of claim 1 wherein the anionic polymerization initiator is metallic potassium.

5. The method of claim 1 wherein the anionic polymerization initiator is metallic lithium.

6. The method of claim 1 wherein an active hydrogen compound is employed to terminate polymerization to provide an inactivated polymer.

7. The method of claim 6 including the step of hydrogenating generally all of the inactivated polymer.

8. The method of claim 1 wherein an agitation means is used to disperse the initiator throughout the reaction mixture.

9. The method of claim 1 wherein the anionic polymerization initiator is an organo-alkali metal compound selected from the group consisting of organo-lithium compounds, organo-sodium compounds and organo-potassium compounds.

10. The method of claim 1 wherein the anionic polymerization initiator is an organo-lithium compound selected from the group consisting of isopropyllithium, n-butyllithium, t-butyllithium, sec-butyllithium, t-octyllithium, n-decyllithium, phenyllithium, naphthyllithium, 4-butylphenyllithium, cyclohexyllithium, 4-butyl-cyclohexyllithium and 4-cyclohexyl-butyllithium.

11. The method of claim 1 wherein the anionic polymerization initiator is n-butyllithium.

12. The method of claim 1 wherein the amount of anionic polymerization initiator is from about 0.01 to about 25.0 mole percent based on amount of 1,3-pentadiene in the mixture of saturated and unsaturated hydrocarbon molecules.

13. The method of claim 1 wherein the inert atmosphere comprises a gaseous element selected from the group consisting of helium, neon, argon, nitrogen and mixtures thereof.

14. The method of claim 11 wherein the polymer of 1,3-pentadiene has polymerized therein three constitutional repeating units:

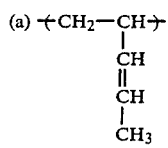  1-2 constitutional repeating unit;

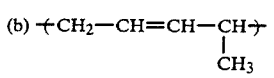  1-4 constitutional repeating unit;

and

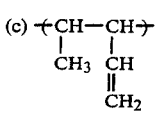  3-4 constitutional repeating unit, said constitutional repeating units being present in amounts based on total amount of constitutional repeating units as follows
(a) from about 37 to about 47 percent,
(b) from about 50 to about 61 percent, and
(c) from about 0.1 to about 6 percent.

15. The method of claim 3 wherein the polymer of 1,3-pentadiene has polymerized therein three constitutional repeating units:

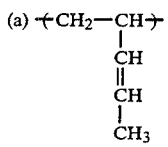  1-2 constitutional repeating unit;

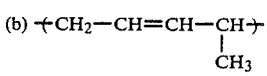  1-4 constitutional repeating unit;

and

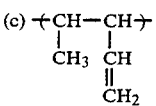  3-4 constitutional repeating unit, said constitutional repeating units being present in amounts based on total amount of constitutional repeating units as follows
(a) from about 54 to about 67 percent,
(b) from about 23 to about 40 percent, and
(c) from about 4 to about 14 percent.

16. The method of claim 5 wherein the polymer of 1,3-pentadiene has polymerized therein three constitutional repeating units:

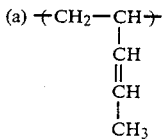  1-2 constitutional repeating unit;

-continued (b) $\vphantom{|}$⁓CH$_2$—CH=CH—CH⁓ 1-4 constitutional repeating unit;
     |
     CH$_3$ and (c) ⁓CH—CH⁓ 3-4 constitutional repeating unit,
    |    |
    CH$_3$ CH
         ‖
         CH$_2$ said constitutional repeating units being present in amounts based on total amount of constitutional repeating units as follows
(a) from about 33 to about 43 percent,
(b) from about 54 to about 64 percent, and
(c) from about 0.1 to about 7 percent.

17. The method of claim 4 wherein the polymer of 1,3-pentadiene has polymerized therein three constitutional repeating units:

(a) ⁓CH$_2$—CH⁓ 1-2 constitutional repeating unit;
         |
         CH
         ‖
         CH
         |
         CH$_3$ (b) ⁓CH$_2$—CH=CH—CH⁓ 1-4 constitutional repeating unit;
                    |
                    CH$_3$ and (c) ⁓CH—CH⁓ 3-4 constitutional repeating unit,
    |    |
    CH$_3$ CH
         ‖
         CH$_2$ said constitutional repeating units being present in amounts based on total amount of constitutional repeating units as follows
(a) from about 43 to about 53 percent,
(b) from about 35 to about 45 percent, and
(c) from about 8 to about 16 percent.

18. A polymer of 1,3-pentadiene, said polymer having polymerized therein three constitutional repeating units:

(a) ⁓CH$_2$—CH⁓ 1-2 constitutional repeating unit;
         |
         CH
         ‖
         CH
         |
         CH$_3$ (b) ⁓CH$_2$—CH=CH—CH⁓ 1-4 constitutional repeating unit;
                    |
                    CH$_3$ and (c) ⁓CH—CH⁓ 3-4 constitutional repeating unit,
    |    |
    CH$_3$ CH
         ‖
         CH$_2$ said constitutional repeating units being present in amounts based on total amount of constitutional repeating units as follows
(a) from about 37 to about 47 percent,
(b) from about 50 to about 61 percent, and
(c) from about 0.1 to about 6 percent.

19. A polymer of 1,3-pentadiene, said polymer having polymerized therein three constitutional repeating units:

(a) ⁓CH$_2$—CH⁓ 1-2 constitutional repeating unit;
         |
         CH
         ‖
         CH
         |
         CH$_3$ (b) ⁓CH$_2$—CH=CH—CH⁓ 1-4 constitutional repeating unit;
                    |
                    CH$_3$ and (c) ⁓CH—CH⁓ 3-4 constitutional repeating unit,
    |    |
    CH$_3$ CH
         ‖
         CH$_2$ said constitutional repeating units being present in amounts based on total amount of constitutional repeating unit as follows
(a) from about 54 to about 67 percent,
(b) from about 23 to about 40 percent, and
(c) from about 4 to about 14 percent.

20. A polymer of 1,3-pentadiene, said polymer having polymerized therein three constitutional repeating units:

(a) ⁓CH$_2$—CH⁓ 1-2 constitutional repeating unit;
         |
         CH
         ‖
         CH
         |
         CH$_3$ (b) ⁓CH$_2$—CH=CH—CH⁓ 1-4 constitutional repeating unit;
                    |
                    CH$_3$ and (c) ⁓CH—CH⁓ 3-4 constitutional repeating unit,
    |    |
    CH$_3$ CH
         ‖
         CH$_2$ said constitutional repeating units being present in amounts based on total amount of constitutional repeating units as follows
(a) from about 33 to about 43 percent,
(b) from about 54 to about 64 percent, and
(c) from about 0.1 to about 7 percent.

21. A polymer of 1,3-pentadiene, said polymer having polymerized therein three constitutional repeating units:

(a) ⁓CH$_2$—CH⁓ 1-2 constitutional repeating unit;
         |
         CH
         ‖
         CH
         |
         CH$_3$ -continued (b) $+CH_2-CH=CH-CH+$  1-4 constitutional repeating unit;
    $\phantom{+CH_2-CH=CH-}|$
    $\phantom{+CH_2-CH=CH-}CH_3$ and (c) $+CH-CH+$  3-4 constitutional repeating unit,
    $\phantom{+}| \phantom{CH} |$
    $\phantom{+}CH_3 \phantom{C} CH$
    $\phantom{+CH_3 CHH} \|$
    $\phantom{+CH_3 CH} CH_2$ said constitutional repeating units being present in amounts based on total amount of constitutional repeating units as follows
(a) from about 43 to about 53 percent,
(b) from about 35 to about 45 percent, and
(c) from about 8 to about 16 percent.

22. A hydrogenated polymer of 1,3-pentadiene, said hydrogenated polymer having polymerized therein three constitutional repeating units (a) $+CH_2-CH+$  1-2 constitutional repeating unit;
    $\phantom{+CH_2-}|$
    $\phantom{+CH_2-}CH_2$
    $\phantom{+CH_2-}|$
    $\phantom{+CH_2-}CH_2$
    $\phantom{+CH_2-}|$
    $\phantom{+CH_2-}CH_3$ (b) $+CH_2-CH_2-CH_2-CH+$  1-4 constitutional repeating unit; and
    $\phantom{+CH_2-CH_2-CH_2-}|$
    $\phantom{+CH_2-CH_2-CH_2-}CH_3$ (c) $+CH-CH+$  3-4 constitutional repeating unit,
    $\phantom{+}| \phantom{CH} |$
    $\phantom{+}CH_3 \phantom{C} CH_2$
    $\phantom{+CH_3 CH} |$
    $\phantom{+CH_3 CH} CH_3$ said constitutional repeating units being present in amounts based on total amount of constitutional repeating units as follows
(a) from about 37 to about 47 percent,
(b) from about 50 to about 61 percent, and
(c) from about 0.1 to about 6 percent.

23. A hydrogenated polymer of 1,3-pentadiene, said hydrogenated polymer having polymerized therein three constitutional repeating units (a) $+CH_2-CH+$  1-2 constitutional repeating unit;
    $\phantom{+CH_2-}|$
    $\phantom{+CH_2-}CH_2$
    $\phantom{+CH_2-}|$
    $\phantom{+CH_2-}CH_2$
    $\phantom{+CH_2-}|$
    $\phantom{+CH_2-}CH_3$ (b) $+CH_2-CH_2-CH_2-CH+$  1-4 constitutional repeating unit; and
    $\phantom{+CH_2-CH_2-CH_2-}|$
    $\phantom{+CH_2-CH_2-CH_2-}CH_3$ (c) $+CH-CH+$  3-4 constitutional repeating unit,
    $\phantom{+}| \phantom{CH} |$
    $\phantom{+}CH_3 \phantom{C} CH_2$
    $\phantom{+CH_3 CH} |$
    $\phantom{+CH_3 CH} CH_3$ said constitutional repeating units being present in amounts based on total amount of constitutional repeating units as follows
(a) from about 54 to about 67 percent,
(b) from about 23 to about 40 percent, and
(c) from about 4 to about 14 percent.

24. A hydrogenated polymer of 1,3-pentadiene, said hydrogenated polymer having polymerized therein three constitutional repeating units (a) $+CH_2-CH+$  1-2 constitutional repeating unit;
    $\phantom{+CH_2-}|$
    $\phantom{+CH_2-}CH_2$
    $\phantom{+CH_2-}|$
    $\phantom{+CH_2-}CH_2$
    $\phantom{+CH_2-}|$
    $\phantom{+CH_2-}CH_3$ (b) $+CH_2-CH_2-CH_2-CH+$  1-4 constitutional repeating unit; and
    $\phantom{+CH_2-CH_2-CH_2-}|$
    $\phantom{+CH_2-CH_2-CH_2-}CH_3$ (c) $+CH-CH+$  3-4 constitutional repeating unit,
    $\phantom{+}| \phantom{CH} |$
    $\phantom{+}CH_3 \phantom{C} CH_2$
    $\phantom{+CH_3 CH} |$
    $\phantom{+CH_3 CH} CH_3$ said constitutional repeating units being present in amounts based on total amount of constitutional repeating units as follows
(a) from about 33 to about 43 percent,
(b) from about 54 to about 64 percent, and
(c) from about 0.1 to about 7 percent.

25. A hydrogenated polymer of 1,3-pentadiene, said hydrogenated polymer having polymerized therein three constitutional repeating units (a) $+CH_2-CH+$  1-2 constitutional repeating unit;
    $\phantom{+CH_2-}|$
    $\phantom{+CH_2-}CH_2$
    $\phantom{+CH_2-}|$
    $\phantom{+CH_2-}CH_2$
    $\phantom{+CH_2-}|$
    $\phantom{+CH_2-}CH_3$ (b) $+CH_2-CH_2-CH_2-CH+$  1-4 constitutional repeating unit; and
    $\phantom{+CH_2-CH_2-CH_2-}|$
    $\phantom{+CH_2-CH_2-CH_2-}CH_3$ (c) $+CH-CH+$  3-4 constitutional repeating unit,
    $\phantom{+}| \phantom{CH} |$
    $\phantom{+}CH_3 \phantom{C} CH_2$
    $\phantom{+CH_3 CH} |$
    $\phantom{+CH_3 CH} CH_3$ said constitutional repeating units being present in amounts based on total amount of constitutional repeating units as follows
(a) from about 43 to about 53 percent,
(b) from about 35 to about 45 percent, and
(c) from about 8 to about 16 percent.

26. A method for anionically preparing polymers of 1,3-pentadiene from a distillation cut available as a by-product of crude oil cracking operations, said distillation cut being a mixture of saturated and unsaturated hydrocarbon molecules, at least 50 percent by weight of said molecules having 5-carbon atoms per molecule, said mixture comprising cis-1,3-pentadiene, trans-1,3-pentadiene, cyclopentadiene and other 5-carbon atom molecules, the method comprising:
(a) forming a reaction mixture by contacting, in an inert atmosphere, the mixture of saturated and unsaturated hydrocarbon molecules with an amount of an alkali metal polymerization initiator, the amount being sufficient to (1) inactivate the chain termination function of generally all cyclopentadiene contained in the mixture and (2) initiate polymerization of 1,3-pentadiene, the alkali metal polymerization initiator having a melting point; and (b) heating the reaction mixture to a temperature, the temperature being (1) greater than or equal to the melting point of the alkali metal polymerization initiator and (2) sufficient to initiate polymerization of 1,3-pentadiene, and dispersing the alkali metal initiator throughout the reaction mixture for a period of time sufficient to attain a desired polymer yield.

27. A method for anionically preparing polymers of 1,3-pentadiene from a distillation cut available as a by-product of crude oil cracking operations, said distillation cut being a mixture of saturated and unsaturated hydrocarbon molecules, at least 50 percent by weight of said molecules having 5-carbon atoms per molecule, said mixture comprising cis-1,3-pentadiene, trans-1,3-pentadiene, cyclopentadiene and other 5-carbon atom molecules, the method comprising:

(a) melting, in an inert atmosphere, an amount of an alkali metal polymerization initiator, the initiator having a melting point and being selected from the group consisting of sodium and potassium, the amount being sufficient to (1) inactivate chain termination functions of generally all cyclopentadiene contained in the distillation cut and (2) initiate polymerization of the 1,3-pentadiene contained in the distillation cut;

(b) heating the distillation cut, in an inert atmosphere, to a temperature, the temperature being greater than or equal to the melting point of the initiator;

(c) dispersing the molten initiator throughout the heated distillation cut to thereby initiate polymerization of 1,3-pentadiene; and (d) maintaining dispersion of the initiator throughout the heated distillation cut for a period of time sufficient to attain a desired polymer yield, the heated distillation cut being maintained at a temperature greater than or equal to the melting point of the initiator.

* * * * *